United States Patent [19]
Leckie et al.

[11] Patent Number: 5,786,149
[45] Date of Patent: Jul. 28, 1998

[54] MATERIALS AND METHODS FOR THE DETECTION OF MYCOBACTERIUM TUBERCULOSIS

[75] Inventors: Gregor W. Leckie, Highland Park; Alan H. Davis, Vernon Hills; Ingrid E. Semple-Facey, Beach Park; Matthew T. Manlove, Vernon Hills; Natalie A. Solomon, Buffalo Grove, all of Ill.

[73] Assignee: Abbott Laboratories, Abbott Park, Ill.

[21] Appl. No.: 774,128

[22] Filed: Dec. 23, 1996

Related U.S. Application Data

[63] Continuation of Ser. No. 242,403, May 13, 1994, Pat. No. 5,631,130.
[51] Int. Cl.⁶ ............................ C12Q 1/68; C12P 19/34; C07H 21/04
[52] U.S. Cl. ..................... 435/6; 435/91.2; 435/91.5; 435/91.52; 435/810; 536/23.7; 536/24.32; 536/24.33; 935/8; 935/17; 935/77; 935/78
[58] Field of Search ................... 435/6, 91.2, 91.5, 435/91.52, 810; 536/23.7, 24.32, 24.33; 935/8, 17, 77, 78

[56] References Cited

FOREIGN PATENT DOCUMENTS

| | | |
|---|---|---|
| 0439182 | 7/1991 | European Pat. Off. |
| 8909835 | 10/1989 | WIPO |
| 9103558 | 3/1991 | WIPO |
| 9300447 | 1/1993 | WIPO |
| 9304201 | 3/1993 | WIPO |

OTHER PUBLICATIONS

Uyemura, K., et al., "Microanatomic clonality of gamma delta T cell in human leishmaniasis Lesions", *Accession No. s80771/Journal of Immunology*, 148:1205-11 (1993).

Rogall, T., et la., "Towards a Phylogeny and Definition of Species at the Molecular Level within the Genus Mycobacterium", *Intern'l Journ. of Ssystematic Bacteriology*, 40:4:323-30 (1990).

Hermans, et al., Insertion Element IS987 from *Mycobacterium bovis* BCG is Located in a Hot-Spot Integration Region for Insertion Elements in *Mycobacterium tuberculosis* Complex Strains, *Infection and Immunity*, 59(8):2695-2705 (1991).

Sjöbring, et al., "Polymerase Chain Reaction for Detection of *Mycobacterium tuberculosis*", *Journal of Clinical Microbiology*, 28(10):2200-2204 (1990).

*Primary Examiner*—Carla J. Myers
*Attorney, Agent, or Firm*—Paul D. Yasger; Thomas D. Brainard

[57] ABSTRACT

The present invention is directed to oligonucleotides useful in detection, e.g., by ligase chain reaction (LCR) of target DNA from *Mycobacterium tuberculosis*. The present invention is also directed to methods of detecting target DNAs from *Mycobacterium tuberculosis*.

5 Claims, 6 Drawing Sheets

FIGURE 1A

| SEQ ID. NO. | | | |
|---|---|---|---|
| | Pab.347-390 Probe Set 1 | | |
| 2 | A | 5' CZ-AACCTGTGGGGTCCGGCCCTTT | GAGAGGTATCCGAACGTCAC-AD 3' |
| 3 | A' | 3' CZ-TTGGACACCCCAGGCCGG | GTGCTCTCCATAGGCTTGCAGTG-AD 5' |
| 4 | B | | |
| 5 | B' | | |
| 1 | Target | 5' AACCTGTGGGGTCCGGCCCTTTCACGAGAGGTATCCGAACGTCAC 3' |
| | Pab. 350-387 Probe Set 2 | | |
| 7 | A | 5' CZ-CTGTGGGGTCCGGCCCTTT | GAGAGGTATCCGAACGT-AD 3' |
| 8 | A' | 3' CZ-GACACCCCAGGCCGG | GTGCTCTCCATAGGCTTGCA-AD 5' |
| 9 | B | | |
| 10 | B' | | |
| 1 | Target | 5' AACCTGTGGGGTCCGGCCCTTTCACGAGAGGTATCCGAACGTCAC 3' |

FIGURE 1B

| SEQ ID. NO. | | | |
|---|---|---|---|
| | Pab. 585-627F Probe Set 5 | | |
| 22 | A | 5' | F-TGAACGGAAAAGTCCTGGCGG                                    ATGTACCAGGGCACCATCAA-B    3' |
| 23 | A' | 3' | F-ACTTGCCTTTTCAGGACCG                                   GGTACATGGTCCCGTGGTAGTT-B    5' |
| 24 | B | | |
| 25 | B' | | |
| 21 | Target | 5' | TGAACGGAAAAGTCCTGGCGGCCATGTACCAGGGCACCATCAAAAACCTG 3' |
| | Pab 585-627 Probe Set 6 | | |
| 26 | A | 5' | CZ-TGAACGGAAAAGTCCTGGCGG                                   ACATGTACCAGGGCACCATCAA-AD   3' |
| 27 | A' | 3' | CZ-ACTTGCCTTTTCAGGACCGCA                                  GGTACATGGTCCCGTGGTAGTT-AD   5' |
| 28 | B | | |
| 29 | B' | | |
| 21 | Target | 5' | TGAACGGAAAAGTCCTGGCGGCCATGTACCAGGGCACCATCAAAAACCTG 3' |
| | Pab.585-633 Probe Set 7 | | |
| 30 | A | 5' | CZ-TGAACGGAAAAGTCCTGGCGGCCA                               ACCAGGGCACCATCAAAAACCTG-AD 3' |
| 31 | A' | 3' | CZ-ACTTGCCTTTTCAGGACCGCC                              ACATGGTCCCGTGGTAGTTTTGGAC-AD 5' |
| 32 | B | | |
| 33 | B' | | |
| 21 | Target | 5' | TGAACGGAAAAGTCCTGGCGGCCATGTACCAGGGCACCATCAAAAACCTG 3' |

FIGURE 1C

| SEQ ID. NO. | | | |
|---|---|---|---|
| | IS987DR.2544-2593 | | |
| | Probe Set 3 | | |
| 12 | A | 5' CZ-CTTGACGCAGTCGTCAGACCCAAAA | 3' |
| 13 | A' | 3' CZ-GAACTGCGTCAGCAGTCTGGG | 5' |
| 14 | B | GAGAGGGGACGGAAACTCGAC-AD | 3' |
| 15 | B' | GGGGCTCTCCCCTGCCTTTGAGCTG-AD | 5' |
| 11 | Target | 5' CTTGACGCAGTCGTCAGACCCAAAACCCCGAGAGGGGACGGAAACTCGAC | 3' |
| | | | |
| | IS6110.535-578 | | |
| | Probe Set 4 | | |
| 17 | A | 5' CZ-GCGAGCTGCGCGATGGCGAA | 3' |
| 18 | A' | 3' CZ-CGCTCGACGCGCTACCGC | 5' |
| 19 | B | AAGGAGCACATCAGCCGCGTC-AD | 3' |
| 20 | B' | GAGTTCCTCGTGTAGTCGGGCGCAG-AD | 5' |
| 16 | Target | 5' GCGAGCTGCGCGATGGCGAACTCAAGGAGCACATCAGCCGCGTC | 3' |

FIGURE 2A

| SEQ ID. NO. | | | |
|---|---|---|---|
| | 16S 690-732.1 Probe Set 15 | | |
| 69 | A | 5' | F-TTCGTGAAAICTCACIGCTT 3' |
| 70 | A' | 3' | F-AAGCACTTTIGAGTGICG 5' |
| 71 | B | | CTGTGIGCCGTGCGGGCGATA-B 3' |
| 72 | B' | | TTGACACICGCACGCCCGCTAT-B 5' |
| 34 | Target | 5' | TGTTCGTGAAATCTCACGGCTTAACTGTGAGCGTGCGGGCGATA 3' |
| | 16S 690-732.1A Probe Set 8 | | |
| 35 | A | 5' CZ or | F-GTTCGTGAAATCTCACGGCTT 3' |
| 36 | A' | 3' CZ or | F-ACAAGCACTTTAGAGTGCCG 5' |
| 37 | B | | CTGTGAGCGTGCGGGCGATA-B or AD 3' |
| 38 | B' | | TTGACACTCGCACGCCCGCTA -B or AD 5' |
| 34 | Target | 5' | TGTTCGTGAAATCTCACGGCTTAACTGTGAGCGTGCGGGCGATA 3' |
| | 16S 690-732.1B Probe Set 16 | | |
| 73 | A | 5' | CZ-GTTCGTGAAAaCTCACaGCTT 3' |
| 74 | A' | 3' | CZ-ACAAGCACTTTtGAGTGtCG 5' |
| 75 | B | | CTGTGgGCCGTGCGGGCGATA-AD 3' |
| 76 | B' | | TTGACACCCGCACGCCCGCTA -AD 5' |

FIGURE 2B

| SEQ ID. NO. | | | |
|---|---|---|---|
| | 16S 721-760 Probe Set 9 | | |
| 40 | A | 5' | F-GTGCGGGCGATACGGGCAGA |
| 41 | A' | 3' | F-CACGCCCGCTATGCCCG |
| 42 | B | 5' | AGAGTACTGCAGGGGAGA-B 3' |
| 43 | B' | 3' | GATCTCATGACGTCCCCTAT-B 5' |
| 39 | Target | 5' | GTGCGGGCGATACGGGCAGACTAGAGTACTGCAGGGAGA 3' |
| | 16S 898-937 Probe Set 10 | | |
| 45 | A | 5' | F-CGCCGTAAACGGTGGGTACT |
| 46 | A' | 3' | F-GCGGGCATTTGCCACCCAT |
| 47 | B | 5' | TGTGGGTTTCCTTCCTT-B 3' |
| 48 | B' | 3' | TCCACACCCAAAGGAAGGAA-B 5' |
| 44 | Target | 5' | CGCCGTAAACGGTGGGTACTAGGTGTGGGTTTCCTTCCTT 3' |
| | 16S 1059-1098 Probe Set 14 | | |
| 65 | A | 5' | F-CAACGCGAAGAACCTTACCT |
| 66 | A' | 3' | F-GTTGCGCTTCTTGGAAT |
| 67 | B | 5' | TTTGACATGCACAGGAC-B 3' |
| 68 | B' | 3' | CCCAAACTGTACGTGTCCTG-B 5' |
| 64 | Target | 5' | CAACGCGAAGAACCTTACCTGGGTTTGACATGCACAGGAC 3' |

FIGURE 2C

| SEQ ID. NO. | | | |
|---|---|---|---|
| | 10kd 477-524 Probe Set 13 | | |
| 60 | A | 5' | F-GGGTGACACCGTCATCTACAGCAA 3' |
| 61 | A' | 3' | F-CCCACTGTGGCAGTAGATGTC 5' |
| 62 | B | | ACGGCGGCACCGAGATCAAGTA-B 3' |
| 63 | B' | | CATGCCGCCGTGGCTCTAGTTCAT-B 5' |
| 59 | Target | 5' | GGGTGACACCGTCATCTACAGCAAGTACGGCGGCACCGAGATCAAGTA 3' |
| | 65kd 244-286 Probe Set 11 | | |
| 50 | A | 5' | F-ACTTCGCAATGGCCAAGACAA 3' |
| 51 | A' | 3' | F-TGAAGCGTTACCGGTTCTG 5' |
| 52 | B | | GCGTACGACGAAGAGGCCCG-B 3' |
| 53 | B' | | AACGCATGCTGCTTCTCCGGGC-B 5' |
| 49 | Target | 5' | ACTTCGCAATGGCCAAGACAATTGCGTACGACGAAGAGGCCCG 3' |
| | 65kd 405-452 Probe Set 12 | | |
| 55 | A | 5' | F-GGTGTGTCCATCGCCAAGGAGATC 3' |
| 56 | A' | 3' | F-CCACACAGGTAGCGGTTCCTCT 5' |
| 57 | B | | CTGGAGGATCCGTACGAGAAG-B 3' |
| 58 | B' | | CTCGACCTCCTAGGCATGCTCTTC-B 5' |
| 54 | Target | 5' | GGTGTGTCCATCGCCAAGGAGATCGAGCTGGAGGATCCGTACGAGAAG 3' |

MATERIALS AND METHODS FOR THE DETECTION OF MYCOBACTERIUM TUBERCULOSIS

This is a continuation of U.S. patent application Ser. No. 08/242,403, filed May 13, 1994, now U.S. Pat. No. 5,631,130.

FIELD OF THE INVENTION

The invention relates to oligonucleotides useful in detecting *M. tuberculosis*. This invention also relates to methods useful in amplifying and/or detecting *M. tuberculosis*.

BACKGROUND OF THE INVENTION

After decades of decline in the incidence of tuberculosis, an alarming increase in new cases is occurring. Infection with *M. tuberculosis*, the causative agent of tuberculosis, most commonly occurs by inhalation of droplets containing only a few live bacilli. The mycobacteria replicate in lung tissue to form a primary focus of infection and from there enter the local lymphatic system. The infection then disseminates widely through the body via the blood and lymphatic system. The initial lesions usually heal to form tiny granulomas that may harbor viable tubercle bacilli indefinitely. Post-primary tuberculosis is the most common form of clinical tuberculosis and is usually pulmonary. The disease can occur many years after initial infection and is thought to be due to a temporary loss or diminishing of cell-mediated immunity (due to, for example, increasing age, illness, malnutrition, or alcoholism) leading to reactivation of dormant tubercle bacilli in lesions. Acquired Immunodeficiency Syndrome (AIDS), increased poverty and its attendant malnutrition are now important factors leading to the increased incidence of the disease.

A tentative diagnosis of tuberculosis or other mycobacterial diseases may be made on a basis of clinical grounds, radiology, and on the finding of acid-fast bacilli in smears of sputum, blood bronchial-lavage, gastric-washing, urine, or cerebral spinal fluid. Smears of these specimens typically are stained by the Ziehl-Neelsen technique or by fluorescent rhodamine-auramine dye and examined by microscopy. However, microscopically positive sputum samples are found in only about 30 to 50 percent of pulmonary tuberculosis patients and thus, cultures must always be performed. Culturing for the presence of *M. tuberculosis* and other mycobacterial species is a time-consuming and difficult process because some mycobacterial species are very slow-growing and have fastidious nutritional requirements. While some samples may be inoculated directly onto culture medium, most specimens require decontamination with, for example, strong alkali. Specimens are then typically inoculated onto egg-based media such as Lowenstein-Jensen medium and/or defined media such as Middlebrook 7H9 broth in the presence of antibiotics such as penicillin to inhibit growth of other bacteria. Cultures are then incubated at 35° C. to 37° C. for 1–7 weeks. However, even culture techniques are only about 70% effective.

Other techniques have also been developed for the detection of *M. tuberculosis*. These methods include nucleic acid hybridization assays using probes directed to nucleic acid sequences found in *M. tuberculosis*. For example, PCT Application No. WO 91/19004 entitled "Specific Detection of *Mycobacterium Tuberculosis*" by Guesdon and Thierry published Dec. 12, 1991 teaches the use of polynucleotide primers corresponding to those found between bases 1–30; 250–275; 1029–1058; 1200–1229; 1260–1289; 1263–1294; 1735–1764 and 1772–1796 of IS 6110, an insertion element present in multiple copies in many *M. tuberculosis* strains as described in Thierry et al. *Nucl. Acids Res.* 18:188 (1990). The application claims sequences derived from IS 6110 and sequences at least 80% homologous thereto. The probes described in that application were used for the detection of *M. tuberculosis* using the polymerase chain reaction.

In PCT Application No. WO 88/03957 published Jun. 25, 1988 by Hogan, et al. a method is described for the detection of non-viral organisms including *M. tuberculosis* and *M. intracellulare* using nucleic acid hybridization techniques. The method comprises constructing an oligonucleotide that is sufficiently complementary to hybridize to a region of ribosomal RNA (rRNA) selected to be unique to a particular non-viral organism or a group of non-viral organisms sought to be detected. The target rRNA is selected by comparing one or more variable region rRNA sequences of the non-viral organisms of interest with one or more variable region rRNA sequences from one or more non-viral organisms sought to be distinguished. Probe sequences which are specific for 16S rRNA variable subsequences of *Mycobacterium avium*, *Mycobacterium intracellulare*, and the *Mycobacterium tuberculosis*-complex bacteria and which do not cross-react with nucleic acids from each other or any other bacterial species under proper stringency are identified. A probe specific to three 23S rRNA variable region subsequences from the *Mycobacteriun tuberculosis*-complex bacteria is also disclosed as are rRNA variable region probes useful in hybridization assays for bacteria of the genus Mycobacterium (15S, 23S rRNA specific); for *Mycobacterium avium* in the region corresponding to bases 185–225 of *E. coli* 16S rRNA; RNA of *Mycobacterium intracellulare* in the region corresponding to bases 185–225 of *E. coli* 16S RNA; to rRNA of the species included in the *Mycobacterium tuberculosis* complex in the region corresponding the bases 185–225 of *E. coli* 16S RNA; to rRNA of the species included in the *Mycobacterium tuberculosis* complex in the region corresponding to the bases 540–575, 1155–1190, and 2195–2235 of *E. coli* 23S RNA; to RNA of the genus Mycobacterium in the region corresponding to 1025–1060 of *E. coli* 16S RNA; and others.

U.S. Pat. No. 4,851,330 by Kohne issued on Jul. 25, 1989, addresses the use of nucleic acid hybridization to detect and quantify non-viral microorganisms. More particularly the patent describes the preparation of cDNA probes which are complementary only to ribosomal RNA subsequences known to be conserved in an organism, category or group of organisms. By way of illustration, the patent describes the production of a cDNA probe complementary to ribosomal RNA from *Mycoplasma hominis* but which was not complementary to human ribosomal RNA. The patent alleges that the *M. hominis* probes are useful in the detection of *M. hominis* contamination in human tissue cultures and in other cultures of mammalian cells.

U.S. Pat. No. 5,168,039 to Crawford et al. is directed to an isolated purified repetitive DNA sequence for use in detecting *M. tuberculosis* complex in clinical material. The patent describes the cloning and sequencing of a repetitive element found in *M. tuberculosis* chromosomal DNA and further describes the use of these cloned repetitive elements as probes and primers for the detection of representative strains of the *M. tuberculosis* complex.

U.S. Pat. No. 5,183,737 to Crawford et al. (divisional of U.S. Pat. No. 5,168,039 described above) teaches the use of the aforementioned repetitive elements as primers for the detection of bacteria of *M. tuberculosis* complex using the polymerase chain reaction. The patent also teaches the use of the repetitive elements as probes for the detection of bacteria of the *M. tuberculosis* complex using a membrane based nucleic acid hybridization assay.

PCT Application WO90/15,157 by Lane et al. published Dec. 13, 1990, addresses "universal" nucleic acid probes for eubacteria and methods for the detection of bacteria. The application describes nucleic acid probes and probe sets which hybridize under specific conditions to the ribosomal RNA molecules (rRNA), rRNA genes (rDNA), and certain amplification and in vitro transcription products thereof but which do not hybridize under the same conditions to rRNA or rDNA of eukaryotic cells which may be present in test samples. More specifically, the probes described in this application are specifically complementary to certain highly conserved bacterial 23S or 16S rRNA sequences. The probes were selected using a computer algorithm operating on aligned sets of 16S and 23S rRNA sequences to identify regions of greatest similarity among the eubacteria Nucleic acid probes so derived hybridize most widely among diverse bacterial species. Probes found homologous among the bacteria species were also assessed for differences with non-bacterial rRNA sequences using a computer algorithm. Ultimately, 41 probes were selected based on these analysis; 22 targeting 23S rRNA and 19 targeting 16S rRNA. The 16S amplification primers described in that application include primers which detect most eubacteria, Borrelia and spirochetes, the enterics, Deinococcus, Campylobacter, and the Fusobacteria and Bacillus species. Several of these probes are assertedly capable of detecting *Mycobacteria kansasii* and *M. bovis*. The application describes the use of sandwich type hybridization assays for the detection of hybridization between probes and rRNAs in samples suspected of containing bacteria and also describes the use of the polymerase chain reaction (PCR) directed to 16S rRNAs using probes as derived above. The probes described in that application (both 16S, and 23S rRNA probes) were assertedly able to detect a wide variety of bacterial species.

PCT application WO90/12,875 by Hance et al. published Nov. 1, 1990 discloses nucleotide sequences of actinomycetales and their application to the synthesis or detection of nucleic acids found in actinomycetales. The application discloses a 383 base pair polynucleotide coding for the 65 kD (kilodalton) mycobacterial antigen which has homologs in 8 species of mycobacteria including *M. tuberculosis, M. avium, M. fortuitum, M. paratuberculosis*, BCG, *M. kansasii, M. malmoense*, and *M. marinum*. The use of these probes for the detection of DNA and/or the products of transcription of these bacteria is described. More particularly, an oligonucleotide comprising bases 397 through 416 of the 65 kD antigen is disclosed (See, Shinnick et al. *Infect. and Immun.* 56:446–451 (1988)). Another sequence corresponding to bases 535 through 554 of the same gene coding for the 65 kD antigen is also disclosed. The application proposes the use of the aforementioned oligonucleotides as primers in the polymerase chain reaction directed toward the detection of mycobacterial species.

European Patent Application No. 0 395 292 by Barry et al. published on Oct. 31, 1990, describes a method for generating DNA probes specific for various microorganisms. Specific probes are disclosed for *Aeromonas hydrophila, Aeromonas salmonicida, Clostridium difficile, Mycobacterium bovis, Mycobacterium tuberculosis, Mycobacterium avium, Salmonella typhimurium*, and other bacteria. A DNA probe for *M. avium* was obtained from a variable intergenic region intermediate the genes coding for 16S ribosomal RNA and 23S ribosomal RNA. DNA probes for *M. bovis* were obtained from a variable intergenic region intermediate the 16S ribosomal RNA gene and the 23S ribosomal rRNA gene and from the V6 variable region of the gene coding for 16S ribosomal RNA. Similarly, a DNA probe for *M. tuberculosis* was obtained from the variable intergenic region intermediate the 16S and 23S ribosomal RNA genes.

The nucleotide sequence of Protein Antigen B gene (pab gene) of *Mycobacterium tuberculosis* was described by Anderson and Hanson, *Inf. and Immun.* 57:2481–2488 (1989). The pab gene is 1993 nucleotides in length. The deduced amino acid sequence of the pab gene reveals 30% homology to a phosphate-binding protein (Ps+S) from *E. coli*. Protein antigen b was selected for analysis because of its association with virulent strains of *M. tuberculosis* and, to a lesser extent, with *M. bovis* BCG and because BCG has been used with some success as a vaccine against tuberculosis. See, e.g., Hart, P. D. and Sutherland, I., *British Medical Tuberculosis Journal* 2:293–295 (1977).

Baird et al. *J. Gen. Microbiol.* 135: 931–939 (1989) have cloned and sequenced the 10 kD antigen gene of *Mycobacterium tuberculosis*. The 10 kD antigen has been implicated (by analogy to the 10 kD protein of *M. bovis*) in the induction of T-cell mediated delayed type hypersensitivity. The 10 kD antigen gene was isolated using a DNA probe corresponding to the N-terminal amino acid sequence of the *M. bovis* 10 kD antigen. This probe was selected because of the demonstrated immunological cross-reactivity between the 10 kD *M. bovis* antigen and the 10 kD antigen of *M. tuberculosis*. Cloning and sequencing of the *M. tuberculosis* 10 kD antigen gene revealed a coding sequence of 300 nucleotides which encode 99 amino acids having an aggregate molecular weight of 10.7 kD. The sequence was shown to be homologous to two procaryotic heat-shock proteins and additionally to have heat-shock like promoter sequences upstream from the initiation codon.

Rogall et al. *Int. J. Syst. Bact.* 40:323–330 sequenced and analyzed the 16S rRNA genes of *M. tuberculosis, M. bovis, M. bovis* BCG, *M. tuberculosis* H37, *M. marinum, M. kansasii* DSM 43224, *M. simiae* ATCC 25275, *M. scrofulaceum* ATCC 19981, *M. szulgai* ATCC 25799, *M. gordonae* ATCC 14470, *M. xenopi* ATCC 19250, *M. flavescens* ATCC 14474, *M. avium* DSM 43216, *M. intracellulare* ATCC 15985, *M. paratuberculosis* ATCC 19698, *M. gastrae* ATCC 15754, *M. malmoense* ATCC 29571, *M. nonchromogenicun* ATCC 19530, *M. terrae* ATCC 15755, *M. chelonae* ATCC 14472, *M. smegmatis* ATCC 14468, *M. fortuitum* ATCC 6841 and *Nocardia asteroides* ATCC 3306. The data obtained from this analysis revealed the phylogenetic relationships between the bacteria. The data showed that the fast growing Mycobacteriun, *M. fortuitum, M. chelonae, M. smegmatis* and *M. flavescens* formed a distinct group separate from all of the other mycobacteria tested. All of the slow-growing mycobacteria species were highly related having similarity values greater than 94.8%.

Hermans et al. *Inf. and Imm.* 59:2695–2705 (1991) determined the sequence of the single copy insertion element IS987 from *M. bovis* BCG. The sequence of IS987 was noted to be virtually identical to the insertion sequence IS986 from *M. tuberculosis* and to reside in a region of the *M. bovis* BCG chromosome containing 20 identical copies of a 36 bp direct repeat, each separated by 35–41 bp of spacer DNA. The data also indicated that IS987 is nearly identical to IS6110 from *M. tuberculosis*, differing in that IS987 has an open reading frame (ORF) designated ORFa in a single ORF whereas IS6110 contains ORFa composed of two different ORFs. These open-reading frames may play a role in the expression of a putative transposase. The data also show that the size and composition of the direct-repeat containing region of the *M. tuberculosis* chromosome is polymorphic and that these repeats were not found in nine other mycobacterial species tested. The authors also suggested that the polymorphism seen in the IS insertion sites allow the easy typing of strains of *M. tuberculosis* complex by restriction fragment length polymorphism analysis.

Thierry et al., *Nucl. Acids Res.* 18:188 (1990) cloned and sequenced the insertion sequence IS6110 from *M. tuberculosis*. The DNA sequence of 1361 nucleotides showed characteristics of insertion sequence (IS) including inverted repeat sequences which are (28 bp in length with 3 mismatched bps and direct 3 bp repeats at each end of the IS element. The authors suggest that this IS element will be useful as a probe for the identification of the *M. tuberculosis* complex.

As noted above, oligonucleotide probes are used for the detection of various microorganisms by means of nucleic acid hybridization using techniques such as dot blot, slot blot, Southern blots, solution hybridization, in situ hybridization and others. Alternatively, the polymerase chain reaction may be used which amplifies the target DNA. U.S. Pat. No. 4,683,195 to Mullis et al. describes the details of the polymerase chain reaction.

Of interest to the background of the invention, is an alternate mechanism for target amplification known as ligase chain reaction (LCR). In LCR, probe pairs are used which include two primary probe partners (first and second probes) and two secondary probe partners (third and fourth) all of which are employed in excess. The first probe of a probe pair hybridizes to a first segment of the target strand and the second probe of a probe pair hybridizes to a second segment of the same target strand, the first and second segments being contiguous so that the primary probes abut one another in 5' phosphate-3' hydroxyl relationship and so that a ligase can covalently fuse or ligate the two probes of the pair into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes will also hybridize to the target complement in the first instance. Once the fused strand of primary probes is separated from the target strand, it will hybridize with the third and fourth probes which can be ligated to form a complementary, secondary fused product. It is important to realize that the fused products are functionally equivalent to either the target or its complement. By repeated cycles of hybridization and ligation, amplification of the target sequence is achieved. This technique is described more completely in K. Backman, et al. EP-A-320 308 published Jun. 14, 1989 and K. Backman, et al., EP-A-439 182 published Jul. 31, 1991, both incorporated by reference in their entirety.

A potential problem associated with ligase chain reaction is background signal caused by target independent ligation of the probes. Since the third probe hybridizes to the first probe and the fourth probe hybridizes to the second probe, the probes, which are added in excess, can easily form duplexes among themselves. These duplexes can become ligated independently of the presence of target to form a fused product which is then indistinguishable from the desired amplified target, yet which is still capable of supporting further amplification. Although target independent blunt-end ligation of these duplexes is a relatively rare event, it is sufficiently common to cause undesirable high background signals in diagnostic assays.

Some attempts to overcome this background problem have been published. For example, WO 90/01069 (Segev Diagnostics) and GB 2 225 112 A (Imperial Chemical Industries Plc.) describe versions of a ligation-based amplification scheme which includes a polymerase-mediated gap-filling step prior to ligation. In addition, EP-A439 182 to K. Backman et al. published Jul. 31, 1991, teaches variations of LCR that reduce background. One such variation involves gap filling and ligation.

In the gap-filling ligation method described in EP-A-439 182 to Backman et al. published Jul. 31, 1991, instead of using probe pairs capable of forming blunt-ended duplexes, at least one probe of a probe pair initially includes a "modified" end which renders the resultant duplex "non-blunt" and/or not a substrate for the ligase catalyzed fusion of the probe pair. A "modified" end is defined with respect to the point of ligation rather than with respect to its complementary probe. A "modified end" has omitted bases to create a "gap" between the terminus of one probe of a probe pair and the terminus of the other probe of a probe pair. Other modifications include mismatches between a probe and a target sequence. "Correction" of the modification is then carried out to render the probes ligatable. "Correction" refers to the process of rendering (in a target dependent manner), the two probes of a probe pair ligatable. Thus, only those probes hybridized to target, target complement or polynucleotide sequences derived therefrom, are corrected. "Correction" can be accomplished in a variety of ways depending on the type of modified end used.

There continues to exist a need in the art for new reagents and methods for the rapid and sensitive detection of *M. tuberculosis* and for bacteria of the genes Mycobacterium.

SUMMARY OF THE INVENTION

The present invention is directed to oligonucleotide probes useful for specific detection of target DNA from Mycobacterium tuberculosis. Such an oligonucleotide probe is from 10 to about 50 nucleotides long and possesses sufficient complementarity or homology to the sequences shown in SEQ ID NOS. 1, 11, 16 or 21 to hybridize with such sequence or its complement under hybridizing conditions, as defined herein. Sufficient complementarity or homology generally requires about 80% to 100% complementarity or homology, preferably 90% or more. Shorter probes typically require higher percentage ranges, while longer probes typically are useful with lower percentage ranges. Preferred are probes in the range of 15 to 40, usually about 20-25 nucleotides in length. Such an oligonucleotide probe preferably does not cross react substantially with other related organisms, including other organisms of the Mycobacterium genus. Preferred examples of such oligonucleotide probes of the invention are the probes of SEQ ID NOS. 2-5, 7-10, 12-15, 17-20 and 22-33.

Another aspect of the present invention includes compositions useful in detecting target DNA from *M. tuberculosis* including: probe set 1 (SEQ ID NOS. 2-5); probe set 2 (SEQ ID NOS. 7-10); probe set 3 (SEQ ID NOS. 12-15); probe set 4 (SEQ ID NOS. 17-20), probe set 5 (SEQ ID NOS. 22-25), probe set 6 (SEQ ID NOS. 26-29), and probe set 7 (SEQ ID NOS. 30-33) as set forth in FIGS. 1A–C and combinations thereof.

Other aspects of the present invention include methods for detecting target DNA from *M. tuberculosis* using the ligase chain reaction using labelled oligonucleotide probes as provided by the compositions of the present invention. The methods of the present invention generally comprise providing a sample suspected of containing said target DNA; providing one or more probe sets according to the compositions of the present invention wherein at least one probe of said probe set has a label capable of detection; and providing one to three deoxynucleotide triphosphates, a polymerase, and a ligase. The following cycle is then performed at least once: mixing said probe set with said sample suspected of containing said target DNA; denaturing said mixture of said probe set and said sample suspected of containing said target DNA; hybridizing said denatured probe set to said denatured target DNA thereby creating hybridized probes; correcting said hybridized probes in a template dependent manner thereby creating adjacent probes; ligating said extended "corrected" adjacent probes using said ligase to form reorganized probes; detecting said label in said reorganized probes. "Correction" as used herein is used in the same sense as in EP 439,182 as incorporated herein by reference.

Additional aspects of the invention include kits useful for the detection of *M. tuberculosis*, the kit comprising suitable containers containing one or more probe sets according to the present invention, and a ligase reagent. Additional kits of the present invention include a ligase reagent, a polymerase reagent, one or more deoxynucleotide triphosphates, one or more probe sets and wherein at least one probe from said probe set has a label.

BRIEF DESCRIPTION OF THE FIGURES

FIG. 1A, 1B and 1C illustrate *M. tuberculosis* species-specific target DNAs and oligonucleotide probes aligned with their respective targets.

FIG. 2A, 2B and 2C illustrate Mycobactedium genus-specific target DNAs and oligonucleotide probes aligned with their respective targets.

In the figures the bases are designated as follows: A=adenine; T=thymine; G=guanine; C=cytosine; and I=inosine. In FIG. 2A, the bases shown in lower case are mismatches with respect to target. Also in the figures the haptens are designated as follows: CZ=carbazole; AD=adamantane; F=fluorescein; B=biotin. Target DNAs are double stranded, though are shown as only a single strand.

DETAILED DESCRIPTION OF THE INVENTION

The oligonucleotide sequences of the present invention are derived from the gene coding for protein antigen B from *M. tuberculosis*, Anderson et al., *Infection and Immunity* 57:2481–2488 (1989); from the direct repeats reported along with insertion element IS987 from *M. bovis*, Hermans et al., *Infection and Immunity* 59:2695–2705; from the insertion-like element IS6110 from *M. tuberculosis*, Thierry et al., *Nucleic Acids Res.* 18:188 (1990), from the 16S ribosomal RNA gene of *M. tuberculosis* according to Rogall et al. (*Int. J. Syst. Bact.* 40:323–330 1990), from the gene coding for 65 kD heat shock protein of *M. tuberculosis* according to Shinnick et al. (*Infect. and Immmun.*, 56:446–451), and from the gene coding for the 10 kD heat shock protein of *M. tuberculosis* according to Baird et al. *J. Gen. Microbiol.* 135:931–939, (1989).

The modified ligase chain reaction (LCR) utilizd in the present invention uses two pairs of probes herein designated A, B (primary probes), and A', B' (secondary probes). Probe pairs as used herein refers to two probes which are directed to the same target strand and which will ultimately be ligated to one another after annealing to the target At least one probe of one of the probe pairs initially includes a "modified" end which renders the resultant duplex "nonblunt" and/or not a suitable substrate for a ligase catalyzed fusion of the two probe duplexes. A "modified end" is defined with respect to the point of ligation rather than with respect to its complementary probe. A "modified end" has omitted bases to create a "gap" between one probe terminus and the next probe terminus when the probe pair is annealed to a target sequence. Other modified ends include a base mismatched with the target sequence.

In most embodiments of the present invention, a modified end is referred to as a "recess", the recess being the gap between two primary or two secondary probes after hybridizing to the target The presence of these modified ends reduces the falsely positive signal created by blunt-end ligation of complementary probe duplexes to one another in the absence of target.

"Correction" of the modification is subsequently carried out to render the probes ligatable. As used herein "correction" refers to the process of rendering, in a target dependent manner, the two primary probes or the two secondary probes ligatable to their partners. Thus, only those probes hybridized to target, target complement or polynucleotide sequences generated therefrom are "corrected." "Correction" can be accomplished by several procedures, depending on the type of modified end used. Gap-filling and nick translation activity are two correction methods described further in the examples.

As used herein, "point of ligation" or "intended point of ligation" refers to a specific location between probe pairs that are to be ligated in a template-dependent manner. It is the site at which the "corrected" probe lies adjacent its partner in 3'-hydroxyl 5'-phosphate relationship. For each set of four LCR probes there are two "points of ligation", a point for the primary probe pair and a point for the secondary probe pair. In conventional LCR the two points of ligation are opposite one another, thus forming blunt ended duplexes when the probe pairs hybridize to one another. In the LCR method used in most embodiments of the present invention, the points of ligation are not opposite one another, but are displaced from one another by one or more bases by virtue of the gaps. The exact point(s) of ligation varies depending on the sequences chosen and, thus is further defined in the context of each embodiment.

Each of the probes comprise deoxyribonucleic acid (DNA) which may be routinely synthesized using conventional nucleotide phosphoramidite chemistry and the instruments available from Applied Biosystems, Inc. (Foster City, Calif.); DuPont, (Wilmington, Del.); or Milligen, (Bedford, Mass.). Phosphorylation of the 5' ends of the appropriate probes, is necessary for ligation by ligase, and may be accomplished by a kinase or by commercial synthesis reagents, as is known in the art.

In general, the LCR methods useful in the practice of the present invention comprise repeated steps of denaturation of the target DNA and (a) hybridizing the modified probes to the target (and, if double stranded so that target complement is present, to the target complement); (b) correcting the modification in a target dependent manner (e.g. filling the gap) to render the probes ligatable; (c) ligating the corrected probe to its partner to form a fused or ligated product; and (d) dissociating the fused product from the target and repeating the hybridization, correction and ligation steps to amplify the desired target sequence. Steps (a), (c) and (d) are essentially the same for all of the embodiments and can be discussed together. Step (b) varies depending on the type of modification employed, but only gap filling and "exo" variations are discussed herein.

"Hybridization" or "hybridizing" conditions is defined generally as conditions which promote nucleation and annealing. It is well known in the art, however, that such annealing is dependent in a rather predictable manner on several parameters, including temperature, ionic strength, probe length and G:C content of the probes. For example, lowering the temperature of the reaction promotes annealing. For any given set of probes, melt temperature, or Tm, can be estimated by any of several known methods. Typically, diagnostic applications utilize hybridization temperatures which are slightly below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased probe length are also known to stabilize duplex formation because G:C pairings involve 3 hydrogen bonds where A:T pairs have just two, and because longer probes have more hydrogen bonds holding the probes together. Thus a high G:C content and longer probe lengths impact the "hybridization conditions" by elevating the melt temperature.

Once probes are selected for a given diagnostic application, the G:C content and length will be known and can be accounted for in determining precisely what "hybridization conditions" will encompass. Since ionic strength is typically optimized for enzymatic activity, the only parameter left to vary is the temperature. For improved specificity, the hybridization temperature is selected slightly below the Tm of the probe; typically 2°–10° C. below the Tm. Thus, obtaining suitable "hybridization conditions" for a particular probe set and system is well within ordinary skill of one practicing this art.

For LCR, the probes are added in approximately equimolar concentration since they are expected to react stoichiometrically. Each probe is generally present in a concentration ranging from about 5 nanomolar (nM) to about 90 nM; preferably from about 10 nM to about 35 nM For a typical reaction volume of 50 μL, this is equivalent to adding from about $3 \times 10^{11}$ to about $1 \times 10^{12}$ molecules of each probe; and around $5 \times 10^{11}$ molecules per 50 has been a good starting point The optimum quantity of probe used for each reaction also varies depending on the number of cycles which must be performed and the reaction volume. Probe concentrations can readily be determined by one of ordinary skill in this art to provide optimum signal for a given number of cycles.

Following provision of the probes, the next step in the LCR method utilized in the present invention is the specific correction step followed by the ligation of one probe of a probe pair to its adjacent partner. Thus, each corrected primary probe is ligated to its associated primary partner and each corrected secondary probe is ligated to its associated secondary partner. An "adjacent" probe is either one of two probes hybridizable with the target in a contiguous orientation, one of which lies with its phosphorylated 5' end in abutment with the 3' hydroxyl end of the partner probe. "Adjacent" probes are created upon correction of the modified end(s) in a target dependent manner. Since enzymatic ligation is the preferred method of covalently attaching two adjacent probes, the term "ligation" will be used throughout the application. However, "ligation" is a general term and is to be understood to include any method of covalently attaching two probes.

The conditions and reagents which make possible the preferred enzymatic ligation step are generally known to those of ordinary skill in the art. Ligating reagents useful in the present invention include T4 ligase, and prokaryotic ligases such as *E. coli* DNA ligase, and *Thermus aquaticus* DNA ligase available from Molecular Biological Resources (Catalog Nos. 107001 and 107002, Milwaukee, Wis.). A thermostable ligase is presently preferred for its ability to maintain activity during the thermal cycling of LCR. Absent a thermally stable ligase, the ligase must be added again each time the cycle is repeated. Also useful are eukaryotic ligases, including DNA ligase of Drosophila, reported by Rabin, et al., *J. Biol. Chem.* 261:10637–10647 (1986).

Once ligated, the fused (reorganized) probe is dissociated (e.g. melted) from the target and, as with conventional LCR, the process is repeated for several cycles. The number of repeat cycles may vary from 1 to about 100, although from about 15 to about 70 are preferred presently.

It is desirable to design probes so that when hybridized to their complementary (secondary) probes, the ends away from the point of intended ligation are not able themselves to participate in other unwanted ligation reactions. Thus, ligatable sticky or blunt ends should be avoided. If such ends must be used, then 5' terminal phosphates should be avoided, eliminated or blocked. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the "wrong" outside ends of the probes can be prevented by blocking the end of at least one of the probes with a "hook" or marker moiety as will be described in detail below. In the absence of one of the above techniques, the outside ends of the probes can be staggered so that if they are joined, they will not serve as template for exponential amplification.

Following amplification, the amplified sequences can be detected by a number of conventional ways known in the art. Typically, detection is performed after separation, by determining the amount of label in the separated fraction. Of course, label in the separated fraction can also be determined subtractively by knowing the total amount of label added to the system and measuring the amount present in the unseparated fraction. Separation may be accomplished by electrophoresis, by chromatography or by the preferred method described below.

In a particularly preferred configuration, haptens, or "hooks" (also referred to as labels), are attached at the available outside ends of at least two probes (opposite ends of fused product), and preferably to the outside ends of all four probes. A "hook" is any moiety having an affinity to a binding partner. Typically, the hook(s) at one end of the fused product (e.g. the 5' end of A and the 3' end of A' comprises an antigen or hapten capable of being immobilied by a specific binding reagent (such as antibody or avidin) coated onto a solid phase. The hook(s) at the other end (e.g. the 3' end of B and the 5' end of B ) contains a different antigen or hapten capable of being recognized by a label or a label system such as an antibody-enzyme conjugate. Exemplary hooks include but are not limited to chromogens, catalysts such as enzymes, luminescent compounds, chemiluminescent compounds, radioactive elements such as $^{32}P$, biotin, fluorescein, digoxin, theophylline, phencyclidine, dansyl, 2-4-dinitrophenol, modified nucleotides such as bromouracil and others, complementary nucleotides, lectinicarbohydrate pairs, enzymes and their co-factors, and others known in the art Other exemplary hooks include adamantane acetic acid as described in U.S. Ser. No. 07/808,508, U.S. Pat. No. 5,464,746 (by Mattingly, P. G., entitled, "Haptens, Tracers, Immunogens and Antibodies for 3-phenyl-1-adamantaneacetic Acids") and carbazole and dibenzofuran derivatives as described in co-owned, co-pending U.S. patent application Ser. No. 07/808,839, U.S. Pat. No. 5,424, 414, (by Fino, J. R., entited, "Haptens, Tracers, Immunogens and Antibodies for Carbazole and Dibenzofuran Derivatives", both filed Dec. 17, 1991 and both of which are incorporated herein by reference.

A method for adding a hapten to the 3'-end of an oligonucleotide is disclosed in co-owned, co-pending U.S. patent application Ser. No. 07/630,908, filed Dec. 20, 1990, now U.S. Pat. No. 5,290,925. Other methods (e.g. Amino Modifier II, Clontech, Palo Alto, Calif.) are known and commercially available for labeling 3' and 5' ends. The method for adding a hapten to the 5' end is through the use of a phosphoramidite reagent as described in Thuong, N. T. et al., *Tet. Letters*, 29(46): 6905–5908 (1988), or Cohen, J. S. et al., U.S. patent application Ser. No. 07/246,688 (NTIS order no. Pat-Appl-7-246,688 (1988)). Thus, exemplary ligated oligonucleotides may have a carbazole at one end and an adamantane at the other end for the detection by the IMx® instrument (Abbott Laboratories, Abbott Park, Ill.) using the microparticle enzyme immunoassay (MEIA) technology. The assay protocol is similar to that used in the commercially available alpha-fetoprotein assay, with the following adaptions: (1) the anti-alpha-fetoprotein antibody coated microparticles are replaced with anti carbazole antibody coated microparticles; and (2) the conjugates of anti-alpha-fetoprotein antibodies:alkaline phosphatase are replaced with the conjugates of anti-3-phenyl-1-adamantaneacetic acid antibodies:alkaline phosphatase.

The protocol for the IMx® MEIA assays is further described in K. Backman et al., EP-A439,182 published Jul. 31, 1991. In brief, the protocol is as follows. A 100 µL of the reaction mixture which has been amplified by LCR is pipetted into the sample well 30 µL of this sample is then pipetted into the incubation well, the anticarbazole antibody coated microparticles are added to the well. An appropriate period of incubation follows which allows the formation of a complex consisting of anticarbazole antibodies and nucleic acid sequences with the carbazole ends. After the incubation, the mixture is pipetted onto the glass fiber capture matrix of the IMx® reaction cell, and antiadamantane antibodies conjugated to alkaline phosphatase are added This leads to a microparticle-oligonucleotide-enzyme complex which will stay on the surface of the glass fiber capture matrix. After the removal of excess reagent in a wash step (throughout this protocol, the blotter beneath the glass fiber capture matrix absorbs reagent solutions which would otherwise overflow the glass fiber capture matrix), the glass-fiber capture matrix is treated with 4-methylumbelliferyl phosphate (MUP). The surface-bound enzyme converts the nonfluorogenic MUP to 4-methylumbellferone (MU), whose fluorescence can be measured. The numerical values given in the following examples are the rate reads of this process, expressed in counts/sec/sec (c/s/s). The amount of ligated probes is directly related to this rate. This concept of MEIA readout of labeled oligonucleotides is described in European Patent Application, publication No. 357,011, published Mar. 7, 1990, "Detection and Amplification of Target Nucleic Acid Sequences," to Laffler, T. G., et al.; and elsewhere.

In the illustrative examples which follow, probe pairs are labeled with a "fluorescein" hapten and a "biotin" hapten or with a "carbazole" hapten and an adamantaneacetic acid ("adamantane") hapten. Typically, "fluorescein" and "biotin" are used together and "adamantane" and "carbazole" are used together in accordance with the description above, although any combination of virtually any haptens would be possible. Preferably, each member of a probe pair has a different label.

In most of the examples, results were read in an IMx® instrument. This is commercially available from Abbott Laboratories (Abbott Park, Ill.) and is described in EP-A-288 793 and in Fiore, M. et al *Clin. Chem.*, 34/9:1726–1732 (1988). It should be noted that the IMx® instrument typically generates "machine" noise or background in the range of 5–12 counts/sec/sec. Other equally suitable methods of detection useful in the practice of the present invention include ELISA, EIA, and immunochromatography and nucleic acid hybridization techniques including southern blotting, dot blotting, slot blotting, solution hybridization and others well known in the art.

Quantities of polymerase are expressed in units, defined as follows: 1 unit of enzyme equals the amount of enzyme required to incorporate 10 nanomoles of total nucleotide into acid-insoluble material in 30 min at 70° C. Units of ligase enzyme are defined herein as: 1 mg of 95% purified *Thermus thermophilus* DNA ligase has a specific activity of about $1\times10^8$ units. While this is not precisely standardized and may vary by as much as 20%, optimization is within the skill of the routine practitioner.

The invention will now be described further by way of examples which are illustrative of the invention and are not intended to limit it in any way. For example, sequences of specific length are listed. It should be understood that sequences covering the same map positions but having slightly fewer or greater numbers of bases are deemed to be equivalents of these sequences and fall within the scope of the invention, provided they will hybridize to the same positions on the target as the listed sequences. It is also understood that sequences having homology to the target sequences of about 80% or more also fall within the scope of the present invention. Preferably any base substitutions in the sequences of the present invention lie 3 or more nucleotides away from the modified ends.

Target sequences and probes were selected so as to include a "stop base" as taught in EP 439 182 by K. Backman et al. published Jul. 21, 1991 to terminate gap filling extension precisely at the point of ligation so that the extended probe abuts its probe partner and can be ligated to it.

For the purposes of the following examples line diluent (LD) is a standard IMx® buffer reagent used to detect machine noise in the absence of target DNA and probe. All data are expressed as IMx® rates of counts/second/second (c/s/s).

EXAMPLE 1

Detection of *M. tuberculosis* Using Probe Set 1 (SEQ ID NOS. 2, 3, 4, and 5)

Probe set 1 (SEQ ID NOS. 2, 3, 4, and 5) was selected to detect a target sequence in *M. tuberculosis* corresponding to nucleotides 347–390 (SEQ ID NO. 1) of the protein antigen b (pab) gene of *M. tuberculosis*. LCR reaction mixtures contained 50 mM EPPS, 30 mM MgCl$_2$, 20 mM K$^+$ (from KOH and KCl) (LCR Buffer), 10 µM NAD, 1.7 µM DATP, and 1.7 µM dCTP (gap fling nucleotides), $1\times10^{12}$ molecules of each oligonucleotide probe, 18,000 units of *Thermus thermophilus* DNA ligase, 2 units Thermus polymerase, (Molecular Biology Resources, Milwaukee, Wis., cat no. 1070.01) 2 µg human placental DNA, and target DNA as set out in Table 1 in a final volume of 200 µl. Cycling was performed on a Perkin-Elmer model 480 thermocycler at the following settings: 93° C. for 1 second; 65° C. for 1 second; then 68° C. for 1 minute 15 seconds for a total of 40 cycles. Probes were labelled with carbazole and adamantane as described above. Following amplification, ligation products were detected using a sandwich immunoassay using an Abbott automated IMx® analyzer as described above.

Table 1 shows the results of LCR using probe set 1 with 10, 25, and 100 molecules of target DNA derived from *M. tuberculosis* Erdman. Table 2 also shows the results of LCR using target DNA, derived from *M. avium*, *M. intracellulare*, *M. kansasii*, and human placental DNA.

TABLE 1

| Target DNA | IMx ® Rate(c/s/s) |
|---|---|
| *M. tuberculosis* Erdman | |
| 10 molecules | 432.9 |
| 25 molecules | 1149.8 |
| 100 molecules | 1636.9 |
| *M. avium* | |
| $10^7$ molecules | 6.5 |
| *M. intracellulare* | |
| $10^7$ molecules | 5.8 |
| *M. kansasii* | |
| $10^7$ molecules | 5.8 |
| Controls | |
| human placental DNA (2 µg) | 5.8 |
| LD | 7.1 |

The results of these experiments show that probe set 1 (SEQ ID NOS. 2, 3, 4, and 5) was capable of detecting as few as 10 molecules of DNA derived from *M. tuberculosis* and showed no cross-reactivity with as many as $10^7$ genomes of DNA derived from *M. avium*, *M. intracellulare*, and *M. kansasii*.

EXAMPLE 2

Detection of *M. tuberculosis* Using Probe Set 2 (SEQ ID NOS. 7, 8, 9 and 10)

Probe set 2 (SEQ ID NOS. 7, 8, 9 and 10) was selected to detect a target sequence in *M. tuberculosis* corresponding to nucleotides 350–387 (SEQ ID NO. 6) of the pab gene of *M. tuberculosis*. LCR was performed as described in Example 1 except that human placental DNA was present at 330 ng/rxn, and cycling was performed on a Perkin-Elmer model 480 thermocycler at the following settings: 94° C., 1 second; 55° C., 1 second; 60° C. for 55 seconds, for a total of 40 cycles. *M. tuberculosis* target DNA was present at 10 molecules/reaction, other target DNAs were present at $1 \times 10^5$ molecules/reaction. Probes were labelled with carbazole and adamantane and detected as above. Results are shown in Table 2.

TABLE 2

| Target DNA | | IMx ® c/s/s |
|---|---|---|
| *M. tuberculosis* | 201 | 266.0 |
| *M. kansasii* | Florisse | 7.3 |
| *M. marinun* | 11564 | 7.5 |
| *M. simiae* | 25273 | 68.5 |
| *M. szulgai* | 23069 | 8.2 |
| *M. xenopi* | 19971 | 7.3 |
| *M. malmoense* | 29571 | 7.5 |
| *M. fortuitum* | 6160 | 7.7 |
| *M. chelonae* | 35752 | 7.2 |
| *M. avium* | Ser. #1 | 7.4 |
| *M. intracellulare* | Howell-P42 | 7.2 |
| *M. intracellulare* | P-54 | 7.5 |

TABLE 2-continued

| Target DNA | | IMx ® c/s/s |
|---|---|---|
| *M. intracellulare* Controls | Ser. 21 | 7.3 |
| human placental DNA (330 ng) | | 7.2 |

Results indicate that probe set 2 (SEQ ID NOS. 7, 8, 9 and 10) was capable of detecting as few as 10 molecules/reaction of *M. tuberculosis* DNA while other target DNAs present at $1 \times 10^5$ molecules/reaction gave little if any detectable signal.

EXAMPLE 3

Detection of *M. tuberculosis* Using Probe Set 3 (SEQ ID NO. 12, 13, 14, and 15)

Probe set 3 (SEQ ID NOS. 12, 13, 14, and 15) was selected to detect a target sequence in *M. tuberculosis* corresponding to nucleotides 2544–2593 (SEQ ID NO. 11) of the direct repeat sequences around IS987. Reactions were performed as described in Example 1 except that the gap filling nucleotides were dCTP and dTTP. Target DNAs and their concentrations are shown in Table 3. In addition, LCR was performed using both $1 \times 10^{12}$ molecules and $2 \times 10^{12}$ molecules of each oligonucleotide probe. LCR cycling was performed on a Perkin-Elmer model 480 thermocycler at the following settings: 93° C., 1 sec; 67° C., 1 sec; 70° C., 1 min 15 sec.

Probes were labelled with carbazole and adamantane as described above and data was obtained using an automated IMx®) analyzer as described above.

TABLE 3

| | IMx ® rate (c/s/s) | |
|---|---|---|
| Target DNA | $1 \times 10^{12}$ mol. probe | $2 \times 10^{12}$ mol. probe |
| *M. tuberculosis* Erdman (25 molecules) | 348.8 | 418.9 |
| *M. tuberculosis* Erdman (100 molecules) | 1174.7 | 419.1 |
| Control | | |
| human placental DNA (2 µg) | 19.7 | 12.7 |

These data illustrate that probe set 3 (SEQ ID NOS. 12, 13, 14, and 15) was capable of detecting 25 and 100 molecules of *M. tuberculosis* target DNA using either $1 \times 10^{12}$ molecules of probe/rxn or $2 \times 10^{12}$ molecules of probe/rxn.

EXAMPLE 4

Detection of *M. tuberculosis* Using Probe Set 4 (SEQ ID NOS. 17, 18, 19, and 20)

Oligonucleotide probe set 4 (SEQ ID NOS. 17, 18, 19, and 20) was selected to detect a target sequence in *M. tuberculosis* corresponding to nucleotides 535–578 (SEQ ID NO.16) of the IS-like element IS6110 of *M. tuberculosis*. In these experiments, reactions were performed as described in Example 1 except that dCTP and dTTP were used for gap filling and cycling was performed in a Perkin-Elmer Model 480 thermocycler at the following settings: 94° C., 1 second; 65° C., 1 second; 70° C., 55 seconds for a total of 40 cycles. Target DNAs and their quantities are shown in Table 4. Reaction products were then cooled and analyzed as described in Example 1. Probes were labelled with carbazole and adamantane as described above.

TABLE 4

| Target DNA | IMx® Rate (c/s/s) | Comment on Data Speed |
|---|---|---|
| M. tuberculosis Erdman (10 molecules) | 607.2 | |
| M. intracellulare 1419 ($10^6$ molecules) | 8.7 | (all 10 samples less than 10) |
| M. avium CSU Ser. #1 ($10^6$ molecules) | 54.5 | (1 sample at 471.4 and 9 samples less than 10) |
| M. kansasii 1203 ($10^6$ molecules) | 15.7 | 1 sample at 84, and 9 samples less than 10) |
| Controls | | |
| human placental DNA (2 µg) | 25.9 | (1 sample each at 526.5, 509.7 and 358.4, and 77 samples less than 10) |
| LD | 6.6 | |

These data illustrate that probe set 4 (SEQ ID NOS. 17, 18, 19, and 20) is capable of detecting as few as 10 molecules of M. tuberculosis target DNA. With the exception of an apparent "outlier", Probe set 4 (SEQ ID NOS. 17, 18, 19, and 20) gave no signal when tested against $10^6$ molecules of target DNA derived from M. intracellulare 1419, M. avium CSU Ser #1 and M. kansasii 1203. Human placental DNA (2 µg) gave an average IMx® Rate of 25.92 c/s/s which is artificially high due to 3 outliers.

EXAMPLE 5

Specificity of Probe Set 5 for M. tuberculosis (SEQ ID NOS. 22, 23, 24 and 25)

Oligonucleotide probe set 5 (SEQ ID NOS. 22, 23, 24 and 25) was selected to detect a target DNA corresponding to nucleotides 585–627 (SEQ ID NO. 21) of the pab gene of M. tuberculosis.

Each reaction was preformed in LCR buffer and contained $5 \times 10^{11}$ molecules of each probe/rxn, 3400 units of ligase, 0.5 units polymerase, 50 ng of human placental DNA, 2000 copies/reaction on of target DNA, all in a final volume of 50 µl. The gap-filling nucleotide was dCIP. Reactions were overlaid with mineral oil and cycling was performed in a COY thermocycler at the following settings: 85° C., 30 sec; 55° C., 20 sec; for 45 cycles. The 50 µl samples were then diluted to 200 µl with IMx® line diluent to provide adequate volume for IMx® operation. Labels were biotin and fluorescein.

Results are shown in Table 5.

TABLE 5

| Target DNA | | IMx® Rate (c/s/s) |
|---|---|---|
| M. tuberculosis | 102 | 1573.5 |
| | 201 | 2130.6 |
| | H37 | 2223.8 |
| | H37RV | 2250.8 |
| | Erdman | 1835.5 |
| M. scrofulaceum | LR130 | 1051.8 |
| | 1302 | 8.1 |
| M. fortuitum | 1547 | 8.9 |
| M. szulgai | CAP | 8.7 |
| M. bovis | 410 | 1688.8 |
| | 401 | 1780.7 |
| | BCG (Glaxo) | 1988.4 |
| M. avium | LR107 | >12.0 |
| | LR163 | >10 |
| | | 9.7 |
| M. intracellulare | LR158 | >10 |
| | LR105 | >10 |
| M. chelonae | 1343 | 8.4 |
| | | 182.6 |
| M. gordonae | 1318 | 8.3 |
| M. terrae | CAP | 8.2 |
| M. phlei | 1516 | 8.7 |
| | | 259.8 |
| M. kansasii | 1214 | 9.4 |
| | | 8.7 |
| M. marinum | 1218 | 9.3 |

The IMx® rate for M. scrofulaceum LR130 in this experiment is suspect because of the wide spread in the data (1687.5 c/s/s and 416.1 c/s/s) and in light of the low average seen for M. scrofulaceum 1302 which gave an average of 8.1 c/s/s. This is possibly due to a contamination of the LR130 sample. Similarly a single, spuriously high reading accounts for the unusually high average IMx® rate seen for M. chelonae which gave IMx® rates of 317.8 c/s/s and 47.5 c/s/s while M. chelonae 1343 gave IMx® rates of only 8.3 c/s/s and 8.4 c/s/s. Similarly, M. phlei gave an unusually high average IMx® rate by virtue of the fact that one of the reactions gave an IMx® rate of 510.5 c/s/s opposed to a rate of 9.1 c/s/s for its duplicate and an average rate of 8.7 c/s/s for M. phlei 1516.

EXAMPLE 6

Detection of M. tuberculosis Using Probe Set 6 (SEQ ID NOS. 26, 27, 28, and 29)

A modification of the LCR method described above was utilized to detect a target sequence corresponding to nucleotides 585–627 (SEQ ID NO. 21) of the protein antigen b (pab) gene of M. tuberculosis using probe set S (SEQ ID NOS. 26, 27, 28, and 29). The LCR method used in this example differs from Example 1 in that it utilizes two sets of blunt-ended probes wherein the 5' end of probe B has a mismatch with the target corrected prior to ligation by 5' to 3' exonuclease activity of the DNA polymerase used in the reaction. This method, variously known as the "exo" or "nick translation" method, the basis for which is described in more detail in co-pending, co-owned U.S. Ser. No. 07/925,402, filed Aug. 3, 1992.

Reaction conditions were those described in Example 1. However, reactions were run using both 2 units of DNA polymerase and 4 units of DNA polymerase in an attempt to determine the effects of increasing polymerase concentration on the efficiency of this variation of LCR. This specific LCR method requires the presence of only one gap-filing nucleotide triphosphate, in this case dCIP. Target DNA was present at 25 molecules per reaction. Cycling was performed in a Perkin-Elmer model 480 thermocycler at the following settings: 93° C., 1 sec.; 62° C., 1 sec; 65° C., 1 min. 30 sec. for 50 cycles. Probes were labelled with carbazole and adamantane. Ligation products were detected using an automated IMx® analyzer as described above. Experiments using 2 units and 4 units of polymerase gave nearly the same average IMx® rates of 1745.7 c/s/s and 1734.3 c/s/s, respectively. Control experiments using only 2 µg of human placental DNA/rxn and 2 and 4 units of polymerase gave nearly the same IMx® rates of 11.32 c/s/s and 12.44 c/s/s, respectively.

EXAMPLE 7

Detection of *M. tuberculosis* Using Probe Set 7 (SEQ ID NOS. 30, 31, 32 and 33)

Oligonucleotide probe set 7 (SEQ ID NOS. 30, 31, 32 and 33) was selected to detect a target DNA corresponding to nucleotides 585–633 (SEQ D NO. 21) of the pab gene of *M. tuberculosis*. LCR was carried out as described in Example 1 with the following exceptions: human placental DNA was present at 300 ng/rxn, dGTP and dTTP were used for gap filling, and cycling was performed in a Perkin-Elmer model 480 thermocycler at the following settings: 93° C., 1 sec; 62° C., 1 sec; 65° C., 1 min. 10 sec for 40 cycles. The probe set was labelled with adamantane and carbazole as described above. Ligation products were detected as described in Example 1. Table 7 shows the results of the assay.

TABLE 7

| Target DNA | IMx ® Rate (c/s/s) |
|---|---|
| *M. tuberculosis* (10 molecules) | 371.7 |
| *M. tuberculosis* (100 molecules) | 1143.4 |
| Control | |
| human placental DNA (330 ng) | 10.8 |

These data show that probe set 7 (SEQ ID NOS. 30, 31, 32, and 33) was capable of detecting as few as 10 molecules of target DNA from *M. tuberculosis*.

EXAMPLE 8

Detection of Bacteria of the Genus Mycobacterium Using Probe Set 9 (SEQ ID NO. 40, 41, 42, and 43)

Oligonucleotides probe set 9 (SEQ ID NOS. 40, 41, 42, and 43) was selected to detect a target sequence corresponding to nucleotides 721–760 of the 16S rRNA gene of *M. tuberculosis* (SEQ ID NO. 39). LCR was performed as described in Example 1 using a Perkin-Elmer Model 480 thermocycler except that cycling was performed at the following settings: 94° C., 1 sec.; 55° C., 1 sec.; 60° C., 40 sec. for a total of 40 cycles. human placental DNA was present at 330 ng/rxn, and each probe was present at 7.5×10¹¹ molecules/reaction. Gap filling nucleotides were dCTP and dTTP. Probes were labelled with fluorescein and biotin respectively. Table 8 shows the results of these assays.

TABLE 8

| Target DNA | | IMx ® Rate (c/s/s) | |
|---|---|---|---|
| | | 100 mol. target | 1000 mol. target |
| *M. tuberculosis* | H37RV | 395.5 | 902.7 |
| | 3508 | 372.2 | 844.5 |
| *M. avium* | 113 | 175.8 | 338.5 |
| | LR147 | 504.2 | 991.9 |
| *M. intracellulare* | LR120 | 352.6 | 604.6 |
| | 1403 | 261.9 | 480.5 |
| *M. scrofulaceum* | LR195 | 205.2 | 536.9 |
| | LR121 | 442.6 | 964.7 |
| *M. kansasii* | 1201 | 160.5 | 583.4 |
| | 1217 | 332.2 | 946.5 |
| *M. chelonae* | 108 | 193.0 | 411.8 |
| | 19977 | 582.2 | 1160.3 |
| *M. fortuitum* | 1545 | 213.7 | 557.9 |
| | 1529 | 234.7 | 671.6 |

TABLE 8-continued

| | IMx ® Rate (c/s/s) | |
|---|---|---|
| Target DNA | 100 mol. target | 1000 mol. target |
| Control | | |
| human placental DNA (330 ng) | | 79.0 |

These results show that probe set 16S 721–760 is capable of detecting numerous species and strains of the genus Mycobacterium.

EXAMPLE 9

Detection of Bacteria of the Genus Mycobacterium Using Probe Set 11 (SEQ ID NOS. 50, 51, 52 and 53)

Oligonucleotide probe set 11 (SEQ ID NOS. 50,51,52, 53) was selected to detect a target sequence corresponding to nucleotides 244–286 of the 65 kD heat shock gene of *M. tuberculosis* (SEQ ID NO.49) with the aim of using the probe set to detect bacteria of the genus Mycobacterium. LCR was performed as described in Example 5 except that the gap filling nucleotide was dTTP. Unless otherwise indicated in Table 9, mycobacterial target DNA was present at 10 pg/rxn which is the equivalent of about 2000 copies of a typical mycobacterial genome. The final reaction volume was 50 µl. Cycling was performed in a COY thermocycler at the following settings: 85° C., 30 sec; 55° C., 20 sec; for 40 cycles. Labels were biotin and fluorescein. Reaction products were analyzed as described in Example 1. Results are shown in Table 9. The data indicate that probe set 11 (SEQ ID NOS. 50,51,52 and 53) detected all of the target DNAs tested except target DNA derived from *M. fortuitum* and *M. terrae*.

TABLE 9

| Target DNA | IMx ® Rate (c/s/s) |
|---|---|
| *M. tuberculosis* (5.0 pg) | 1243.5 |
| *M. avium* LR107 | 934.3 |
| LR163 | 374.9 |
| *M. scrofulaceum* LR130 | 1045.5 |
| *M. intracellulare* LR158 | 571.6 |
| LR105 | 921.3 |
| *M. bovis* | 789.6 |
| *M. tuberculosis* | 916 |
| *M. tuberculosis* | 1507.7 |
| *M. hemophilus* | 1057.3 |
| *M. szulgai* | 838.8 |
| *M. fortuitum* | 52.6 |
| *M. tuberculosis* | 860.9 |
| *M. marinum* | 1031.3 |
| *M. scrofulaceum* | 731.6 |
| *M. kansasii* | 765.7 |
| *M. tuberculosis* | 1320.1 |
| *M. phlei* | 317.7 |
| *M. bovis* | 1177.5 |
| *M. gordonae* | 308.1 |
| *M. chelonae* | 427.6 |
| *M. terrae* | 9.9 |
| *M. malmoense* | 705.6 |
| *M. bovis* BCG Glaxo | 1510.3 |

EXAMPLE 10

Detection of Bacteria of the Genus Mycobacterium Using Probe Set 12 (SEQ ID NOS. 55, 56, 57 and 58)

Oligonucleotide probe set 12 (SEQ ID NOS. 55, 56, 57, and 58) was selected to detect a target sequence corresponding to nucleotides 405–452 of the 65 kD heat shock gene (SEQ ID NO. 54) of *M. tuberculosis* with the aim of using the probe set as a probe for bacteria of the genus Mycobacterinum. LCR was performed as described in Example 1 except that the gap filling nucleotides were DATP and dGTP, human placental DNA was present at 330 ng/rxn, each probe was present at $6\times10^{12}$ probes/rxn, and cycling was performed on a Perkin-Elmer model 480 thermocycler at the following settings: 94° C., 1 sec.; 55° C., 1 sec.; and 60° C., 55 sec., for a total of 40 cycles. Probes were labelled with biotin and fluorescein respectively.

Reaction products were then analyzed by the automated IMx® procedure described in Example 1. The results of these experiments are shown in Table 10. Target DNAs and their amounts are listed in Table 10.

TABLE 10

| Target DNA ($10^4$ molecules/reaction) | IMx Rate (c/s/s) |
|---|---|
| *M. tuberculosis* 201 | 495.6 |
| *M. avium* LR163 | 123 |
| *M. intracellulare* LR158 | 213.2 |
| human placental DNA | 10.2 |
| LD | 9.9 |

The data indicate that probe set 12 (SEQ ID NOS. 55, 56, 57, and 58) was capable of detecting 10,000 molecules each of genomic DNA from *M. tuberculosis*, *M. avium*, and *M. intracellulare*.

EXAMPLE 11

Detection of Bacteria of the Genus Mycobacterium Using Probe Set 13 (SEQ ID NOS. 60, 61, 62 and 63)

Oligonucleotide probe set 13 (SEQ ID NOS. 60, 61, 62, and 63) was selected to detect a target DNA corresponding to nucleotides 477–524 (SEQ ID NO 59) of the 10 kD heat-shock protein gene from *M. tuberculosis*. LCR was performed as described in Example 1 except that the gap filling nucleotides were dTTP and dGTP, probes were present at $2\times10^{11}$ molecules each, and cycling was performed on a Perkin-Elmer model 480 thermocycler at the following settings: 94° C., 1 sec.; 60° C., 1 sec.; and 65° C., 55 sec., for 40 cycles. Probes were labelled with carbazole and adamantane respectively. Reaction products were then analyzed by the automated IMx® procedure described in Example 1. Target DNAs and their amounts are listed in Table 11. The results of these experiments are summarized in Table 11.

TABLE 11

| Target DNA | | IMx ® Rate (c/s/s) | |
|---|---|---|---|
| | | 1000 molecules | 100 molecules |
| *M. tuberculosis* | H37RV | 2240.7 | 1632.4 |
| | 35801 | 1935.6 | 1237.2 |
| *M. avium* | 113 | 1495.7 | 661.0 |
| | 146 | 1917 | 1074.4 |
| *M. intracellulare* | 120 | 1889.8 | 993.2 |
| | 1430 | 1417.3 | 385.1 |
| *M. scrofulaceum* | 195 | 2083.5 | 1120.8 |
| | 121 | 2040.7 | 1307 |
| *M. kansasii* | 1201 | 1753.5 | 735.8 |
| | 1217 | 1820.4 | 909 |
| *M. chelonae* | 108 | 875.3 | 177.8 |
| | 19977 | 1302.2 | 396.1 |
| *M. fortuitum* | 1545 | 1716.4 | 649.1 |
| | 1529 | 1235.9 | 646.8 |

TABLE 11-continued

| Target DNA | IMx ® Rate (c/s/s) | |
|---|---|---|
| | 1000 molecules | 100 molecules |
| Controls | | |
| human placental DNA (330 ng) | 93.5 | |
| LD | 11.9 | |

These data indicate that probe set 13, 54 (SEQ ID NOS. 60, 61, 62, and 63) was capable of detecting as few as 100 molecules of target DNA derived from the mycobacterial species and strains tested. In addition, the probe set gave little or no signal when used in reactions containing human placental DNA.

EXAMPLE 12

Detection of Bacteria of the Genus Mycobacterium Using Probe Set 14 (SEQ ID NOS. 65, 66, 67 and 68)

Oligonucleotide probe set 14 (SEQ ID NOS. 65, 66, 67, and 68 were selected to detect a target DNA corresponding to nucleotides 1059–1098 (SEQ ID NO. 64) of the *M. tuberculosis* 16S ribosomal RNA gene. LCR assays were performed as described in Example 1 except probes were present at $5\times10^{11}$ molecules each and the reaction contained 330 ng human placental DNA. Gap filling nucleotides were dATP and dGTP. Probes were labelled with biotin and fluorescein respectively. Cycling was performed in a Perkin-Elmer Model 480 Thermocycler at the following settings: 94° C., 1 sec; 57° C., 1 sec; 62° C., 25 sec; for a total of 40 cycles. Reaction products were analyzed as described in Example 1. Results are shown in Table 12.

TABLE 12

| Target DNA (1000 Molecules) | | IMx Rate c/s/s |
|---|---|---|
| *M. tuberculosis* | H37RV | 792.7 |
| | 35801 | 387.4 |
| *M. avium* | 113 | 186.3 |
| | LR147 | 440 |
| *M. intracellulare* | LR120 | 373.1 |
| | 1403 | 152.5 |
| *M. scrofulaceum* | LR195 | 622.1 |
| | LR121 | 495.6 |
| *M. kansaii* | 1201 | 279.5 |
| | 1277 | 560.7 |
| *M. chelonae* | 108 | 261.2 |
| | 1977 | 1048.6 |
| *M. fortuitum* | 1545 | 374.5 |
| | 1529 | 333.6 |
| Controls | | |
| LD | | 9.7 |
| human placental DNA (330 ng) | | 30.8 |

The results indicate that the probe set 14 (SEQ ID NOS 65, 66, 67 and 68) set was capable of detecting 1,000 molecules of all of the target DNAs tested.

EXAMPLE 13

Detection of Bacteria of the Genus Mycobacterium Using Probe Set 15 (SEQ ID NOS. 69, 70, 71 and 72)

Oligonucleotide probe set 15 (SEQ ID NOS. 69, 70,71 and 72) was used to detect a target DNA corresponding to nucleotides 690–732 (SEQ ID NO.34) of the 16S ribosomal RNA of *M. tuberculosis* (and others). LCR was carried out as described in Example 5 except that the gap-filling nucleotide was dATP, and $2\times10^{12}$ molecules of each probe was used. Probes were labelled with biotin and fluorescein. Reactions were overlaid with mineral oil and reactions were cycled in a COY thermocycler at the following settings: 85° C. for 30 sec; 40° C. for 30 sec; for 45 cycles. Reaction products were analyzed as described in Example 1. Results are shown in Table 13.

TABLE 13

| Target DNA (1 ng) | | IMx ® Rate (c/s/s) |
|---|---|---|
| M. tuberculosis | 35801P | 487.2 |
| M. tuberculosis | 27294 | 611.7 |
| M. tuberculosis | 35801E | 590.6 |
| M. tuberculosis | 25681 | 391.7 |
| M. avium | LR113 | 735.7 |
| M. avium | LR150 | 1159.1 |
| M. avium | 25291 | 82.6 |
| M. smegmatis | 19420 | 102.0 |
| M. fortuitum | 12478 | 264.5 |
| Controls | | |
| Calf thymus DNA (100 ng) | | 2.5 |
| E. coli DNA (50 ng) | | 7.4 |

These results indicate that probe set 15 was capable of detecting target DNA from at least four species from the genus Mycobacterium.

EXAMPLE 14

Detection of Bacteria of the Genus Mycobacterium Using Probe Set 8 (SEQ ID NOS. 35, 36, 37, and 38)

Oligonucleotide probe set 8 (SEQ ID NOS. 35, 36, 37, and 38) was selected to detect a target DNA corresponding to nucleotides 690–732 (SEQ ID NO 34) of the 16S ribosomal RNA gene of M. tuberculosis (and others). LCR was carried out as described in Example 5 except that probes were present at $2\times10^{12}$ molecules/reaction, and cycling was performed at: 85° C., 30 sec; 55° C. for 30 sec; for a total of 45 cycles. Reaction products were analyzed as described in Example 1. Probes were labelled with biotin and fluorescein, respectively. Results are shown in Table 14.

TABLE 14

| Target DNA (5 pg) | | IMx ® Rate (c/s/s) |
|---|---|---|
| M. intracellulare | LR158 | 558.5 |
| M. gordonae | 1318 | 188.0 |
| M. malmoense | 802 | 228.1 |
| M. terrae | CAP | 15.0 |
| M. avium | LR107 | 440.1 |
| M. haemophilum | | 405.0 |
| M. kansasii | 1214 | 137.1 |
| M. scrofulaceum | 1302 | 318.7 |
| M. marinum | 1218 | 662.8 |
| M. tuberculosis | 102 | 294.0 |
| M. szulgai | | 193.9 |
| Control | | |
| human placental DNA (1 µg) | | 9.7 |

These results show that probe set 8 was capable of detecting target DNA from several species of bacteria of the genus Mycobacterium. However, this probe set failed to detect target DNA from M. terrae.

EXAMPLE 15

Detection of Bacteria of the Genus Mycobacterium Using Probe Set 16 (SEQ ID NOS. 73, 74, 75 and 76)

Oligonucleotide probe set 16 (SEQ ID NOS. 73, 74, 75 and 76) was selected to detect a target DNA of the 16S ribosomal RNA gene of various mycobacteria LCR was performed as described in Example 1 using DATP as the gap-filling nucleotide, and $2\times10^{12}$ molecules of each probe. Thermocycling was performed in a Sutter Dunker at the following settings: 85° C. for 85 sec; 62° C. for 120 sec; for a total of 40 cycles.

Reaction products were analyzed as described in Example 1. Results are shown in Table 15.

TABLE 15

| | IMx ® Rate | |
|---|---|---|
| Target DNA | 100 Molecules of Target | 1,000 Molecules of Target |
| M. chelonae | 889.3 | 1381.5 |
| M. avium | 63.2 | 53.5 |
| M. terrae | 920.1 | 1380.0 |
| M. phlei | 935.1 | 1341.0 |
| M. tuberculosis | 35.9 | 305.1 |
| M. avium | 74.2 | 11.1 |
| M. intracellulare | 118.5 | 205.6 |
| Control | | |
| human placental DNA (330 ng) | 25.02 | |
| LD | 9.97 | |

These data indicate that probe set 16 (SEQ ID NOS. 73, 74, 75, and 76) was capable of detecting a subset of target DNAs from bacteria of the genus Mycobacteriun.

EXAMPLE 16

Detection of Bacteria of the Genus Mycobacterium with Probes from Probe Sets 8 (SEQ NOS. 35, 36, 37, and 38) and 16 (SEQ ID NOS. 73, 74, 75 and 76).

Probes from oligonucleotide probe sets 8 (SEQ ID NOS. 35, 36, 37, and 38), and 16 (SEQ ID NOS. 73, 74, 75 and 76) were selected to detect a target sequence corresponding to the 16S ribosomal RNA gene of various mycobacteria. LCR was performed as described in Example 1 except that cycling was performed in a Sutter dunker at 85° C. for 55 sec. followed by 62° C. for 85 sec. for a total of 40 cycles. Reaction products were analyzed as described in Example 1. Probes were labelled with carbazole and adamantane as described previously. Human placental DNA was present at 330 ng/reaction.

The following groups of probes were used:

Group 1:
Probe A (SEQ ID NO. 35), and A' (SEQ ID NO. 36) from Set 8 (GSM1A);
Probe A (SEQ ID NO. 73), and A' (SEQ ID NO. 74) from Set 16 (GSM1B).

Group 2:
Probe B (SEQ ID NO. 75), and B' (SEQ ID NO. 76) from Set 16 (GSM1B).

Group 3:
Probe A (SEQ ID NO. 35), probe A' (SEQ ID NO. 36), probe B (SEQ ID NO. 37), probe B' (SEQ ID NO. 38) from Set 8 GSM1A.

Table 16 shows the combination of probes used, and their concentrations.

TABLE 16

| Trial | Group 1 | Group 2 | Group 3 |
|---|---|---|---|
| 1 | $2.5 \times 10^{12}$/rxn | $2.5 \times 10^{12}$/rxn | |
| 2 | $3.5 \times 10^{12}$/rxn | $2.5 \times 10^{12}$/rxn | |

TABLE 16-continued

| Trial | Group 1 | Group 2 | Group 3 |
|---|---|---|---|
| 3 | $4.5 \times 10^{12}$/rxn | $2.5 \times 10^{12}$/rxn | |
| 4 | $2.5 \times 10^{12}$/rxn | $3.5 \times 10^{12}$/rxn | |
| 5 | $3.5 \times 10^{12}$/rxn | $3.5 \times 10^{12}$/rxn | |
| 6 | $4.5 \times 10^{12}$/rxn | $3.5 \times 10^{12}$/rxn | |
| 7 | | | $3.5 \times 10^{12}$/rxn |
| 8 | | | $4.5 \times 10^{12}$/rxn |
| 9 | | | $5.5 \times 10^{12}$/rxn |

TABLE 17

| Trial | M. tuberculosis c/s/s | M. chelonae c/s/s | human placental DNA c/s/s |
|---|---|---|---|
| 1 | 387.3 | 1045.3 | 18.7 |
| 2 | 635.9 | 1145.1 | 132.3 |
| 3 | 699.4 | 1133.4 | 116.4 |
| 4 | 389.0 | 1142.1 | 680.4 |
| 5 | 588.4 | 1144.9 | 288.7 |
| 6 | 671.2 | 1149.5 | 204.4 |
| 7 | 440.7 | | 25.1 |
| 8 | 551.7 | | 24.4 |
| 9 | 654.2 | | 9.5 |

Results derived using each of these combinations are shown in Table 17, and illustrate that the combined probe sets of group 1 and 2 detected both M. tuberculosis and M. chelonae.

EXAMPLE 17

Detection of Bacteria of the Genus Mycobacterium Using A Mixture of Probe Set 8 (SEQ ID NOS. 35, 36, 37, and 38) and Probe Set 16 (SEQ ID NOS. 73, 74, 75 and 76)

Oligonucleotide probe set 8 (SEQ ID NOS. 35, 36, 37, and 38) and oligonucleotide probe set 16 (SEQ ID NOS. 73, 74, 75 and 76) were used together to detect a target DNA corresponding to the 16S ribosomal RNA gene of various mycobacteria. LCR was performed as described in Example 5 except that all 8 probes were present at $5 \times 10^{11}$ molecules/reaction, and cycling was performed at in a COY thermocycler at the following settings: 55° C., 30 sec., 85° C., 20 sec. for a total of 45 cycles. Reaction products were analyzed as described in Example 1. Probes were labelled with biotin and fluorescein. Results are shown in Table 18.

TABLE 18

| Target DNA (5 pg) | IMx ® Rate (c/s/s) |
|---|---|
| M. avium | 444.9 |
| M. gordonae 1318 | 329.2 |
| M. malmoense 802 | 724.4 |
| M. terrae CAP | 1458.5 |
| M. chelonae | 1213.6 |
| M. haemophilum | 898.2 |
| M. kansasii 1214 | 661.6 |
| M. scrofulaceum 302 | 578.5 |
| M. marinum 1218 | 911.6 |
| M. phlei | 1144.7 |
| M. szulgai C | 563.5 |
| Control | |
| human placental DNA | 52.1 |

These results show that the combination of probe sets 8 (SEQ ID NOS. 35, 36, 37, and 38) and 16 (SEQ ID NOS. 73, 74, 75 and 76) was capable of detecting target DNA from all of the species of bacteria of the genus Mycobacterium tested.

EXAMPLE 18

Detection of Bacteria of the Genus Mycobacterium With Probes From Probe Set 8 (SEQ ID NOS. 35, 36, 37 and 38) and 16 (SEQ ID NOS. 73, 74, 75 and 76)

As can be seen in FIG. 2A, the three differences between GSM1A (Probe Set 8) and GSM1B (Probe Set 16) reside at two locations in A/A' and one location B/B'. As was suggested by the previous examples, the two probe sets detect different subsets of the mycobacteria. Therefore, in an attempt to better detect both subsets, probes from GSM1A and GSM1B were combined in different ratios and used as probes for the detection of a wide variety of mycobacterial species.

In a preferred method, the A/A' pairs of GSM1A and GSM1B were combined in a ratio of 2:1, respectively, with the concentration of total A/A'=B/B'.

LCR was performed as in Example 1 except that the amount of oligonucleotide probes were as follows: GSM1A A/A' was $2.67 \times 10^{12}$/rxn, GSM1B A/A' was $1.33 \times 10^{12}$/rxn, GSM1B B/B' was $4 \times 10^{12}$/rxn, and human placental DNA was present at 330 ng/rxn. Cycling was performed in a Sutter dunker at 85° C. for 85 sec., 62° C. for 85 sec., for a total of 40 cycles. Reaction products were detected as described in Example 1. Mycobacterial target DNA was present at 100 copies/rxn. Non-mycobacterial target DNAs were present at 10 ng/rxn (about $1 \times 10^6$ molecules). Probes were labelled with carbazole and adamantane as described above. Results are shown in Table 19.

TABLE 19

| Target DNA | IMx ® Rate (c/s/s) |
|---|---|
| M. tuberculosis 201 | 278.6 |
| M. chelonae | 170.1 |
| M. aurum | 36.6 |
| M. terrae | 226.1 |
| M. phlei | 161.8 |
| M. gordonae | 219.7 |
| M. scrofulaceum | 335.0 |
| M. marinum | 321.5 |
| M. fortuitum | 352.4 |
| M. malmoense | 192.0 |
| M. szulgai | 177.1 |
| M. bovis | 128.9 |
| M. scrofulaceum 1302 | 213.2 |
| M. haemophilus | 155.9 |
| M. smegmatis | 274.0 |
| M. kansasii | 57.2 |
| M. avium LR107 | 55.9 |
| M. intracellulare LR158 | 510.5 |
| M. intracellulare LR105 | 212.2 |
| M. tuberculosis 102 | 197.7 |
| M. bovis 410 | 302.3 |
| MBCG Glaxo | 264.1 |
| M. avium LR163 | 552.3 |
| Citrobacter freundii | 31.1 |
| Enterobacter cloacae | 29.6 |
| E. coli | 47.0 |
| Salmonella interitidus | 58.1 |
| Shigella sonei | 22.7 |
| Klebsiella pneumoniae | 53.7 |
| Pseudomonas aeruginosa | 19.6 |
| Corynebacter renale | 15.9 |
| N. dassonvillei | 66.0 |
| N. asteroides | 31.6 |
| N. brasiliensus | 22.8 |
| Staphlococcus aureus | 63.1 |
| Streptococcus pyrogenes | 30.5 |
| human placental (330 ng) | 25.9 |
| LD | 9.3 |

These results show that the combination of probe set 8 (SEQ ID NOS. 35, 36, 37, and 38) and probe set 16 (SEQ ID NOS. 73, 74, 75 and 76) was capable of detecting target DNA from a wide variety of bacteria of the genus Mycobacteriun.

The foregoing examples are presented by way of illustration and are not intended to limit the scope of the invention as set forth in the appended claims. For example, sequences of specific length are listed. It should be understood that sequences covering the same map positions but having slightly fewer or greater numbers of bases are deemed to be equivalents of these sequences and fall within the scope of the invention, provided they will hybridize to the same positions on the target as the listed sequences.

We claim:

1. A composition for detecting a target DNA sequence from *Mycobacterium tuberculosis*, wherein:

a) said composition comprises a probe set selected from the group consisting of probe set 1 (SEQ ID NOS. 2–5), and probe set 2 (SEQ ID NOS. 7–10);

b) said target DNA sequence from *Mycobacterium tuberculosis* is SEQ ID NO. 21 or its complement; and c) said probe set, does not detect *Mycobacterium avium*.

2. A method for detecting the presence of target DNA from *Mycobacterium tuberculosis* in a sample, said method utilizing the ligase chain reaction comprising the steps of:

a) providing a sample suspected of containing said target DNA;

b) providing one or more probe sets according to claim 1, wherein at least one probe of said probe set has a label capable of detection;

c) providing a ligase, one or more deoxynucleotide triphosphates and a polymerase; and d) performing the following cycle at least once
   i) hybridizing said probe set to said target DNA thereby creating hybridized probes,
   ii) correcting at least one of said hybridized probes in a template dependent manner,
   iii) ligating said hybridized probes to form reorganized probes, and
   iv) detecting said label in said reorganized probes as an indication of the presence of target DNA from *Mycobacterium tuberculosis*.

3. The method of claim 2 wherein said label comprises a specific binding partner.

4. The method of claim 3 wherein said ligase and said polymerase are thermostable.

5. A kit useful in the detection of target DNA from *Mycobacterium tuberculosis*, said kit comprising one or more containers containing a probe set selected from the group consisting of probe set 1 (SEQ ID NOS. 2–5), and probe set 2 (SEQ ID NOS. 7–10); wherein said probe sets are specific for SEQ. ID No. 21 or its complement and said probe sets do not detect *Mycobacterium avium*.

* * * * *

SEQUENCE LISTING ( 1 ) GENERAL INFORMATION:

( i i i ) NUMBER OF SEQUENCES: 76

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( x i ) SEQUENCE DESCRIPTION: SEQ ID NO:1:

AACCTGTGGG GTCCGGCCTT TCACGAGAGG TATCCGAACG TCAC        44

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:2:

AACCTGTGGG GTCCGGCCTT T        21

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:3:

GGCCGGACCC CACAGGTT        18

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:4:

GAGAGGTATC CGAACGTCAC        20

( 2 ) INFORMATION FOR SEQ ID NO:5:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:5:

GTGACGTTCG GATACCTCTC GTG     23

( 2 ) INFORMATION FOR SEQ ID NO:6:
    (Omitted since it is a duplication of SEQ ID No 1)

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:7:

CTGTGGGGTC CGGCCTTT     18

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:8:

GGCCGGACCC CACAG     15

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:9:

GAGAGGTATC CGAACGT     17

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:10:

ACGTTCGGAT ACCTCTCGTG     20

( 2 ) INFORMATION FOR SEQ ID NO:11:

( i ) SEQUENCE CHARACTERISTICS:
        ( A ) LENGTH: 50 base pairs (B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: M. Bovis BCG (xi) SEQUENCE DESCRIPTION: SEQ ID NO:11:

CTTGACGCAG TCGTCAGACC CAAAACCCCG AGAGGGGACG GAAACTCGAC  50

(2) INFORMATION FOR SEQ ID NO:12:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:12:

CTTGACGCAG TCGTCAGACC CAAAA  25

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:13:

GGGTCTGACG ACTGCGTCAA G  21

(2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:14:

GAGAGGGGAC GGAAACTCGA C  21

(2) INFORMATION FOR SEQ ID NO:15:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:15:

GTCGAGTTTC CGTCCCCTCT CGGGG  25

(2) INFORMATION FOR SEQ ID NO:16:

(i) SEQUENCE CHARACTERISTICS:
(A) LENGTH: 44 base pairs
(B) TYPE: nucleic acid
(C) STRANDEDNESS: double ( D ) TOPOLOGY: linear ( i i ) MOLECULE TYPE: DNA (genomic)

( v i ) ORIGINAL SOURCE:
            ( A ) ORGANISM: Mycobacterium tuberculosis ( x i ) SEQUENCE DESCRIPTION: SEQ ID NO:16:

GCGAGCTGCG CGATGGCGAA CTCAAGGAGC ACATCAGCCG CGTC 44

( 2 ) INFORMATION FOR SEQ ID NO:17:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: synthetic DNA ( x i ) SEQUENCE DESCRIPTION: SEQ ID NO:17:

GCGAGCTGCG CGATGGCGAA 20

( 2 ) INFORMATION FOR SEQ ID NO:18:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: synthetic DNA ( x i ) SEQUENCE DESCRIPTION: SEQ ID NO:18:

CGCCATCGCG CAGCTCGC 18

( 2 ) INFORMATION FOR SEQ ID NO:19:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: synthetic DNA ( x i ) SEQUENCE DESCRIPTION: SEQ ID NO:19:

AAGGAGCACA TCAGCCGCGT C 21

( 2 ) INFORMATION FOR SEQ ID NO:20:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: synthetic DNA ( x i ) SEQUENCE DESCRIPTION: SEQ ID NO:20:

GACGCGGCTG ATGTGCTCCT TGAG 24

( 2 ) INFORMATION FOR SEQ ID NO:21:

( i ) SEQUENCE CHARACTERISTICS:
            ( A ) LENGTH: 49 base pairs
            ( B ) TYPE: nucleic acid
            ( C ) STRANDEDNESS: double
            ( D ) TOPOLOGY: linear ( i i ) MOLECULE TYPE: DNA (genomic)

( v i ) ORIGINAL SOURCE:
    ( A ) ORGANISM: Mycobacterium tuberculosis ( x i ) SEQUENCE DESCRIPTION: SEQ ID NO:21:

TGAACGGAAA AGTCCTGGCG GCCATGTACC AGGGCACCAT CAAAACCTG     49

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:22:

TGAACGGAAA AGTCCTGGCG G     21

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:23:

GCCAGGACTT TTCCGTTCA     19

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:24:

ATGTACCAGG GCACCATCAA     20

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:25:

TTGATGGTCC CTGGTACATG G     21

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:26:

TGAACGGAAA AGTCCTGGCG G    21

(2) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:27:

ACGCCAGGAC TTTTCCGTTA C    21

(2) INFORMATION FOR SEQ ID NO:28:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:28:

ACATGTACCA GGGGCACCAT CAA    23

(2) INFORMATION FOR SEQ ID NO:29:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:29:

TTGATGGTGC CCTGGTACAT GG    22

(2) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:30:

TGAACGGAAA AGTCCTGGCG GCCA    24

(2) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:31:

CCGCCAGGAC TTTTCCGTTC A    21

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:32:

ACCAGGGCAC CATCAAAACC TG       22

( 2 ) INFORMATION FOR SEQ ID NO:33:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:33:

CAGGTTTTGA TGGTGCCCTG GTACA       25

( 2 ) INFORMATION FOR SEQ ID NO:34:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium ( x i ) SEQUENCE DESCRIPTION: SEQ ID NO:34:

TGTTCGTGAA ATCTCACGGC TTAACTGTGA GCGTGCGGGC GATA       44

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:35:

TGTTCGTGAA ATCTCACGGC TT       22

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:36:

GCCGTTCAGA TTTCACGAAC A       21

( 2 ) INFORMATION FOR SEQ ID NO:37:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: Synthetic DNA ( x i ) SEQUENCE DESCRIPTION: SEQ ID NO:37:

CTGTGAGCGT GCGGGCGATA  20

( 2 ) INFORMATION FOR SEQ ID NO:38:

: ( i ) SEQUENCE CHARACTERISTICS:
:: ( A ) LENGTH: 22 base pairs
:: ( B ) TYPE: nucleic acid
:: ( C ) STRANDEDNESS: single
:: ( D ) TOPOLOGY: linear : ( i i ) MOLECULE TYPE: Synthetic DNA : ( x i ) SEQUENCE DESCRIPTION: SEQ ID NO:38:

TATCGCCCGC ACGCTCACAG TT  22

( 2 ) INFORMATION FOR SEQ ID NO:39:

: ( i ) SEQUENCE CHARACTERISTICS:
:: ( A ) LENGTH: 40 base pairs
:: ( B ) TYPE: nucleic acid
:: ( C ) STRANDEDNESS: double
:: ( D ) TOPOLOGY: linear : ( i i ) MOLECULE TYPE: DNA (genomic)

: ( v i ) ORIGINAL SOURCE:
:: ( A ) ORGANISM: Mycobacterium tuberculosis

: ( x i ) SEQUENCE DESCRIPTION: SEQ ID NO:39:

GTGCGGGCGA TACGGGCAGA CTAGAGTACT GCAGGGGAGA  40

( 2 ) INFORMATION FOR SEQ ID NO:40:

: ( i ) SEQUENCE CHARACTERISTICS:
:: ( A ) LENGTH: 20 base pairs
:: ( B ) TYPE: nucleic acid
:: ( C ) STRANDEDNESS: single
:: ( D ) TOPOLOGY: linear : ( i i ) MOLECULE TYPE: Synthetic DNA : ( x i ) SEQUENCE DESCRIPTION: SEQ ID NO:40:

GTGCGGGCGA TACGGGCAGA  20

( 2 ) INFORMATION FOR SEQ ID NO:41:

: ( i ) SEQUENCE CHARACTERISTICS:
:: ( A ) LENGTH: 17 base pairs
:: ( B ) TYPE: nucleic acid
:: ( C ) STRANDEDNESS: single
:: ( D ) TOPOLOGY: linear : ( i i ) MOLECULE TYPE: Synthetic DNA : ( x i ) SEQUENCE DESCRIPTION: SEQ ID NO:41:

GCCCTGATCG CCCGCAC  17

( 2 ) INFORMATION FOR SEQ ID NO:42:

: ( i ) SEQUENCE CHARACTERISTICS:
:: ( A ) LENGTH: 18 base pairs ( B ) TYPE: nucleic acid
      ( C ) STRANDEDNESS: single
      ( D ) TOPOLOGY: linear ( i i ) MOLECULE TYPE: Synthetic DNA ( x i ) SEQUENCE DESCRIPTION: SEQ ID NO:42:

AGAGTACTGC AGGGGAGA                                                               18

( 2 ) INFORMATION FOR SEQ ID NO:43:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Synthetic DNA ( x i ) SEQUENCE DESCRIPTION: SEQ ID NO:43:

TATCCCCTGC AGTACTCTAG                                                             20

( 2 ) INFORMATION FOR SEQ ID NO:44:

( i ) SEQUENCE CHARACTERISTICS:
      ( A ) LENGTH: 40 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Mycobacterium ( x i ) SEQUENCE DESCRIPTION: SEQ ID NO:44:

CGCCGTAAAC GGTGGGTACT AGGTGTGGGT TTCCTTCCTT                                       40

( 2 ) INFORMATION FOR SEQ ID NO:45:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Synthetic DNA ( x i ) SEQUENCE DESCRIPTION: SEQ ID NO:45:

CGCCGTAAAC GGTGGGTACT                                                             20

( 2 ) INFORMATION FOR SEQ ID NO:46:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: Synthetic DNA ( x i ) SEQUENCE DESCRIPTION: SEQ ID NO:46:

TACCCACCGT TTACGGCG                                                               18

( 2 ) INFORMATION FOR SEQ ID NO:47:

( i ) SEQUENCE CHARACTERISTICS:
      ( A ) LENGTH: 17 base pairs
      ( B ) TYPE: nucleic acid
      ( C ) STRANDEDNESS: single (D) TOPOLOGY: linear (i i) MOLECULE TYPE: Synthetic DNA (x i) SEQUENCE DESCRIPTION: SEQ ID NO:47:

TGTGGGTTTC CTTCCTT 17

(2) INFORMATION FOR SEQ ID NO:48:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:48:

AAGGAAGGAA ACCCACACCT 20

(2) INFORMATION FOR SEQ ID NO:49:

(i) SEQUENCE CHARACTERISTICS:
(A) LENGTH: 43 base pairs
(B) TYPE: nucleic acid
(C) STRANDEDNESS: double
(D) TOPOLOGY: linear (i i) MOLECULE TYPE: DNA (genomic)

(v i) ORIGINAL SOURCE:
(A) ORGANISM: Mycobacterium (x i) SEQUENCE DESCRIPTION: SEQ ID NO:49:

ACTTCGCAAT GGCCAAGACA ATTGCGTACG ACGAAGAGGC CCG 43

(2) INFORMATION FOR SEQ ID NO:50:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:50:

ACTTCGCAAT GGCCAAGACA A 21

(2) INFORMATION FOR SEQ ID NO:51:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:51:

GTCTTGGCCA TTGCGAAGT 19

(2) INFORMATION FOR SEQ ID NO:52:

(i) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: Synthetic DNA ( x i ) SEQUENCE DESCRIPTION: SEQ ID NO:52:

GCGTACGACG AAGAGGCCCG    20

( 2 ) INFORMATION FOR SEQ ID NO:53:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:53:

CGGGCCTCTT CGTCGTACGC AA    22

( 2 ) INFORMATION FOR SEQ ID NO:54:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium ( x i ) SEQUENCE DESCRIPTION: SEQ ID NO:54:

GGTGTGTCCA TCGCCAAGGA GATCGAGCTG GAGGATCCGT ACGAGAAG    48

( 2 ) INFORMATION FOR SEQ ID NO:55:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:55:

GGTGTGTCCA TCGCCAAGGA GATC    24

( 2 ) INFORMATION FOR SEQ ID NO:56:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:56:

TCTCCTTGGC GATGGACACA CC    22

( 2 ) INFORMATION FOR SEQ ID NO:57:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:57:

CTGGAGGATC CGTACGAGAA G
21

( 2 ) INFORMATION FOR SEQ ID NO:58:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:58:

CTTCTCGTAC GGATCCTCCA GCTC
24

( 2 ) INFORMATION FOR SEQ ID NO:59:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium ( x i ) SEQUENCE DESCRIPTION: SEQ ID NO:59:

GGGTGACACC GTCATCTACA GGAAGTACGG CGGCACCGAG ATC
43

( 2 ) INFORMATION FOR SEQ ID NO:60:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:60:

GGGTGACACC GTCATCAACA GCAA
24

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:61:

CTGTGATGAC GGTGTCACCC
20

( 2 ) INFORMATION FOR SEQ ID NO:62:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:62:

ACGGCGGCAC CGAGATCAAG TA 22

(2) INFORMATION FOR SEQ ID NO:63:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Synthetic DNA (xi) SEQUENCE DESCRIPTION: SEQ ID NO:63:

TAGTTTCATC TCGGTGCCGC CGTAC 25

(2) INFORMATION FOR SEQ ID NO:64:

(i) SEQUENCE CHARACTERISTICS:
(A) LENGTH: 40 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium (xi) SEQUENCE DESCRIPTION: SEQ ID NO:64:

CAACGCGAAG AACCTTACCT GGGTTTGACA TGCACAGGAC 40

(2) INFORMATION FOR SEQ ID NO:65:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Synthetic DNA (xi) SEQUENCE DESCRIPTION: SEQ ID NO:65:

CAACGCGAAG AACCTTACCT 20

(2) INFORMATION FOR SEQ ID NO:66:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Synthetic DNA (xi) SEQUENCE DESCRIPTION: SEQ ID NO:66:

TAAGGTTCTT CGCGTTG 17

(2) INFORMATION FOR SEQ ID NO:67:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Synthetic DNA (xi) SEQUENCE DESCRIPTION: SEQ ID NO:67:

TTTGACATGC ACAGGAC 17

( 2 ) INFORMATION FOR SEQ ID NO:68:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:68:

GTCCTGTGCA TGTCAAACCC            20

( 2 ) INFORMATION FOR SEQ ID NO:69:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Synthetic DNA ( i x ) FEATURE:
        ( A ) NAME/KEY: N stands for inosine
        ( B ) LOCATION: positions 10 and 16

( x i ) SEQUENCE DESCRIPTION: SEQ ID NO:69:

TTCGTGAAAN CTCACNGCTT            20

( 2 ) INFORMATION FOR SEQ ID NO:70:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Synthetic DNA ( i x ) FEATURE:
        ( A ) NAME/KEY: N stands for inosine
        ( B ) LOCATION: positions 3 and 9

( x i ) SEQUENCE DESCRIPTION: SEQ ID NO:70:

GCNGTGAGNT TTCACGAA            18

( 2 ) INFORMATION FOR SEQ ID NO:71:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Synthetic DNA ( i x ) FEATURE:
        ( A ) NAME/KEY: N stands for inosine
        ( B ) LOCATION: position 6

( x i ) SEQUENCE DESCRIPTION: SEQ ID NO:71:

CTGTGNGCGT GCGGGCGATA            20

( 2 ) INFORMATION FOR SEQ ID NO:72:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Synthetic DNA ( i x ) FEATURE:
  ( A ) NAME/KEY: N stands for inosine
  ( B ) LOCATION: position 15

( x i ) SEQUENCE DESCRIPTION: SEQ ID NO:72:

TATCGCCCGC ACGCNCACAG TT  22

( 2 ) INFORMATION FOR SEQ ID NO:73:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:73:

GTTCGTGAAA ACTCACAGCT T  21

( 2 ) INFORMATION FOR SEQ ID NO:74:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:74:

GCTGTGAGTT TTCACGAACA  20

( 2 ) INFORMATION FOR SEQ ID NO:75:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:75:

CTGTGGGCGT GCGGGCGATA  20

( 2 ) INFORMATION FOR SEQ ID NO:76:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:76:

ATCGCCCGCA CGCCCACAGT T  21